(12) United States Patent
Furukawa et al.

(10) Patent No.: US 9,382,227 B2
(45) Date of Patent: Jul. 5, 2016

(54) PHENYLETHANOLAMINE-BASED NMDA RECEPTOR ANTAGONISTS

(71) Applicant: Cold Spring Harbor Laboratory, Cold Spring Harbor, NY (US)

(72) Inventors: Hiro Furukawa, Cold Spring Harbor, NY (US); Erkan Karakas, Huntington, NY (US)

(73) Assignee: Cold Spring Harbor Laboratory, Cold Spring Harbor, NY (US)

( * ) Notice: Subject to any disclaimer, the term of this patent is extended or adjusted under 35 U.S.C. 154(b) by 36 days.

(21) Appl. No.: 14/146,230

(22) Filed: Jan. 2, 2014

(65) Prior Publication Data

US 2014/0200244 A1  Jul. 17, 2014

Related U.S. Application Data

(62) Division of application No. 13/353,992, filed on Jan. 19, 2012, now Pat. No. 8,648,198.

(60) Provisional application No. 61/434,421, filed on Jan. 19, 2011.

(51) Int. Cl.

| | |
|---|---|
| *C07D 401/06* | (2006.01) |
| *C07D 211/14* | (2006.01) |
| *C07D 211/18* | (2006.01) |
| *C07D 211/22* | (2006.01) |
| *G01N 33/566* | (2006.01) |
| *A61K 31/4422* | (2006.01) |
| *G01N 33/68* | (2006.01) |
| *G06F 19/16* | (2011.01) |

(52) U.S. Cl.
CPC .......... *C07D 401/06* (2013.01); *A61K 31/4422* (2013.01); *C07D 211/14* (2013.01); *C07D 211/18* (2013.01); *C07D 211/22* (2013.01); *G01N 33/566* (2013.01); *G01N 33/6896* (2013.01); *G06F 19/16* (2013.01); *G01N 2333/70571* (2013.01); *G01N 2500/20* (2013.01)

(58) Field of Classification Search
CPC .................................................... C07D 401/06
USPC ........................................................ 514/323
See application file for complete search history.

(56) References Cited

U.S. PATENT DOCUMENTS

| | | | |
|---|---|---|---|
| 5,338,754 | A | 8/1994 | Chenard |
| 5,455,250 | A | 10/1995 | Chenard |
| 5,594,007 | A | 1/1997 | Chenard |
| 5,716,961 | A | 2/1998 | Sands |
| 6,046,213 | A | 4/2000 | Chenard et al. |
| 6,667,317 | B2 | 12/2003 | Chenard et al. |
| 6,821,985 | B2 | 11/2004 | Chenard et al. |
| 6,958,351 | B2 | 10/2005 | Chenard et al. |
| 2002/0072485 | A1 | 6/2002 | Chenard et al. |
| 2003/0129134 | A1 | 7/2003 | Chenard et al. |
| 2009/0137686 | A1 | 5/2009 | Rothaul et al. |

FOREIGN PATENT DOCUMENTS

| | | |
|---|---|---|
| EP | 0 768 086 A1 | 4/1997 |
| JP | 2012-102069 A | 5/2012 |
| WO | WO 96/37226 A2 | 11/1996 |
| WO | WO 01/89447 A2 | 11/2001 |

OTHER PUBLICATIONS

Clayton et al., Crystal structure of the GluR2 amino-terminal domain provides insights into the architecture and assembly of ionotropic glutamate receptors. J Mol Biol. Oct. 9, 2009;392(5):1125-32. doi: 10.1016/j.jmb.2009.07.082. Epub Aug. 3, 2009.
Ewald et al., Cloning and Phylogenetic Analysis of NMDA Receptor Subunits NR1, NR2A and NR2B in *Xenopus laevis* Tadpoles. Front Mol Neurosci. 2009;2:4. doi: 10.3389/neuro.02.004.2009. Epub Sep. 11, 2009.
Gallagher et al., Interactions between ifenprodil and the NR2B subunit of the N-methyl-D-aspartate receptor. J Biol Chem. Apr. 19, 1996;271(16):9603-11. PubMed PMID: 8621635.
Gielen et al., Mechanism of differential control of NMDA receptor activity by NR2 subunits. Nature. Jun. 4, 2009;459(7247):703-7. doi: 10.1038/nature07993.
Gotti et al., Ifenprodil and SL 82.0715 as cerebral anti-ischemic agents. I. Evidence for efficacy in models of focal cerebral ischemia. J Pharmacol Exp Ther. Dec. 1988;247(3):1211-21.

(Continued)

*Primary Examiner* — David K. O'Dell
(74) *Attorney, Agent, or Firm* — Wolf, Greenfield & Sacks, P.C.

(57) ABSTRACT

Described herein are enhanced N-methyl-D-aspartate (NMDA) receptor antagonists, pharmaceutical compositions thereof, and their methods of use and treatment, e.g., of Formula (I):

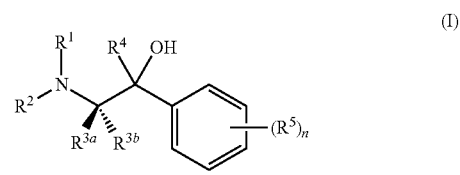

wherein one or more of $R^1$, $R^2$, $R^3$, $R^4$, $R^5$, or the ring formed by the joining of $R^1$ and $R^2$, is a hydrophobic moiety which confers enhanced antagonist activity as compared to existing NMDA receptor antagonists, e.g., ifenprodil. Compounds described herein are designed based on the discovery that ifenprodil binds within the allosteric domain of the GluN1/GluN2B NMDA receptor, particularly at the interface between GluN1 and GluN2B subunits. In silico methods are further described herein.

4 Claims, 25 Drawing Sheets

(56) References Cited

OTHER PUBLICATIONS

Hansen et al., Control of assembly and function of glutamate receptors by the amino-terminal domain. Mol Pharmacol. Oct. 2010;78(4):535-49. doi: 10.1124/mol.110.067157. Epub Jul. 21, 2010.

Jin et al., Crystal structure and association behaviour of the GluR2 amino-terminal domain. EMBO J. Jun. 17, 2009;28(12):1812-23. doi: 10.1038/emboj.2009.140. Epub May 21, 2009.

Karakas et al., Structure of the zinc-bound amino-terminal domain of the NMDA receptor NR2B subunit. EMBO J. Dec. 16, 2009;28(24):3910-20. doi: 10.1038/emboj.2009.338.

Karakas et al., Subunit arrangement and phenylethanolamine binding in GluN1/GluN2B NMDA receptors. Nature. Jun. 15, 2011;475(7355):249-53. doi: 10.1038/nature10180.

Koller et al., Novel N-methyl-D-aspartate receptor antagonists: a review of compounds patented since 2006. Expert Opin Ther Pat. Dec. 2010;20(12):1683-702. doi:10.1517/13543776.2010.533656. Epub Nov. 8, 2010.

Kumar et al., The N-terminal domain of GluR6-subtype glutamate receptor ion channels. Nat Struct Mol Biol. Jun. 2009;16(6):631-8. doi: 10.1038/nsmb.1613. Epub May 24, 2009.

Lee et al., Amino terminal domains of the NMDA receptor are organized as local heterodimers. PLoS One. Apr. 22, 2011;6(4):e19180. doi:10.1371/journal.pone.0019180.

Malherbe et al., Identification of critical residues in the amino terminal domain of the human NR2B subunit involved in the RO 25-6981 binding pocket. J Pharmacol Exp Ther. Dec. 2003;307(3):897-905.

Masuko et al., A regulatory domain (R1-R2) in the amino terminus of the N-methyl-D-aspartate receptor: effects of spermine, protons, and ifenprodil, and structural similarity to bacterial leucine/isoleucine/valine binding protein. Mol Pharmacol. Jun. 1999;55(6):957-69.

Mercer et al., $^{125}$I-ifenprodil: synthesis and characterization of binding to a polyamine-sensitive site in cerebral cortical membranes. J Neurochem. Jul. 1993;61(1):120-6. PubMed PMID: 8515257.

Mony et al., Allosteric modulators of NR2B-containing NMDA receptors: molecular mechanisms and therapeutic potential. Br J Pharmacol. Aug. 2009;157(8):1301-17. doi: 10.1111/j.1476-5381.2009.00304.x. Epub Jul. 8, 2009.

Perin-Dureau et al., Mapping the binding site of the neuroprotectant ifenprodil on NMDA receptors. J Neurosci. Jul. 15, 2005;22(14):5955-65.

Rachline et al., The micromolar zinc-binding domain on the NMDA receptor subunit NR2B. J Neurosci. Jan. 12, 2005;25(2):308-17.

Schmidt et al., Molecular and functional characterization of Xenopus laevis N-methyl-d-aspartate receptors. Mol Cell Neurosci. Oct. 2009;42(2):116-27. doi: 10.1016/j.mcn.2009.06.004. Epub Jun. 12, 2009.

Sobolevsky et al., X-ray structure, symmetry and mechanism of an AMPA-subtype glutamate receptor. Nature. Dec. 10, 2009;462(7274):745-56. doi: 10.1038/nature08624.

Traynelis et al., Glutamate receptor ion channels: structure, regulation, and function. Pharmacol Rev. Sep. 2010;62(3):405-96. doi: 10.1124/pr.109.002451.

Williams, Ifenprodil discriminates subtypes of the N-methyl-D-aspartate receptor: selectivity and mechanisms at recombinant heteromeric receptors. Mol Pharmacol. Oct. 1993;44(4):851-9.

PHENYLETHANOLAMINE-BASED NMDA RECEPTOR ANTAGONISTS

CROSS-REFERENCE TO RELATED APPLICATIONS

The present application is a divisional of and claims priority under 35 U.S.C. §120 to U.S. patent application, U.S. Ser. No. 13/353,992, filed Jan. 19, 2012, now U.S. Pat. No. 8,648, 198, which claims priority under 35 U.S.C. §119(e) to U.S. Provisional Patent Application, U.S. Ser. No. 61/434,421, filed Jan. 19, 2011, each of which is incorporated herein by reference.

GOVERNMENT FUNDING

This application was made with government support under Grant No. 5R01MH085926-02, awarded by the National Institutes of Health. The United States Government has certain rights in the invention.

BACKGROUND OF THE INVENTION

Neurotransmission mediated by N-methyl-D-aspartate (NMDA) receptors is essential for the basic brain development and function (Traynelis et al., 2010). These glutamate receptors predominantly control synaptic plasticity and memory function. NMDA receptors form heteromeric ion channels and activate upon concurrent binding of glycine and glutamate to the GluN1 and GluN2 subunits, respectively. Their ion channel activity is allosterically regulated by binding of small compounds to the amino terminal domain (ATD) in a subtype specific manner.

Since the unexpected discovery that the anti-hypertensive agent, ifenprodil, has neuroprotective effect through NMDA receptors (Gotti et al., 1988), enormous effort has been made to understand the mechanism of its pharmacological action of and to improve compound design for therapeutic purposes (Hansen et al., 2010; Mony et al., 2009). Despite such studies, the structural determinants responsible for NMDA receptor subunit selectivity have not been identified. Consequently, the design and development of additional therapeutic phenylethanolamine-based compounds for use as neuroprotectants have been limited.

SUMMARY OF THE INVENTION

The present invention provides for NMDA receptor antagonists which exhibit greater NMDA activity than that of ifenprodil.

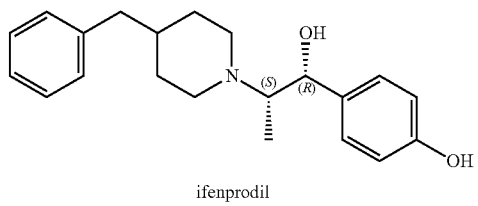

ifenprodil

The subject NMDA receptor antagonists are referred to herein as enhanced NMDA receptor antagonists. It is understood herein that the enhanced NMDA receptor antagonist is not ifenprodil or a pharmaceutically acceptable salt thereof. Compounds disclosed herein are useful for the treatment of any condition in which reduced NMDA receptor function is desirable, such as for the treatment of neuropathies and neurological disorders and disease.

Further described herein is the atomic map of the binding site of ifenprodil within the allosteric domain of the GluN1/GluN2B NMDA receptor, particularly at the interface between GluN1 and GluN2B subunits. The X-ray coordinates of this complex have been published by the inventors of the present Application, See, e.g., Karakas, Simorowski and Furukawa, Nature Letter (2011) 475:249-253 and accompanying Supplementary Information, the entirety of each of which is incorporated herein by reference. The atomic map shows that GluN1 and GluN2B form a heterodimer at the ATD of the NMDA receptor, and that ifenprodil binds at the GluN1-GluN2B subunit interface, rather than within GluN2B alone, as was previously thought. The crystal structure of the GluN1b/GluN2B ATD heterodimer shows a pattern of subunit arrangements that differs from that observed in homodimeric non-NMDA receptors and reveals the molecular determinants for binding of ifenprodil, thus providing a guide for the development of enhanced NMDA receptor antagonists which are phenylethanolamine-based compounds. For example, the present invention contemplates using the X-ray coordinates obtained from these studies of GluN1-GluN2B ifenprodil binding for in silico methods of designing enhanced NMDA receptor antagonists.

In one aspect, provided are enhanced NMDA receptor antagonists which are phenylethanol amine-based compounds of Formula (I):

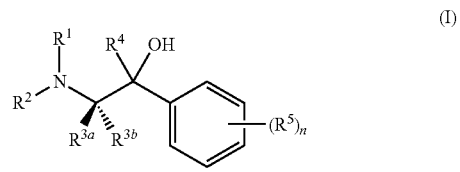

or pharmaceutically acceptable salt thereof;
wherein:
$R^1$ and $R^2$ are independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, and an amino protecting group, provided both $R^1$ and $R^2$ are not each hydrogen, or $R^1$ and $R^2$ are joined to form an optionally substituted heterocyclic or optionally substituted heteroaryl ring;

$R^{3a}$, $R^{3b}$, and $R^4$ are independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, and optionally substituted heteroaryl;

each instance of $R^5$ is independently selected from the group consisting of hydroxyl, substituted hydroxyl, thio, substituted thio, amino, primary amino, secondary amino, sulfonyl, sulfinyl, carbonyl, silyl, boronyl, phosphino, halo, optionally substituted alkyl, optionally substituted alkenyl, optionally substituted alkynyl, optionally substituted carbocyclyl, optionally substituted heterocyclyl, optionally substituted aryl, and optionally substituted heteroaryl; and n is 0 or an integer between 1 and 5, inclusive;

provided at least one of $R^1$, $R^2$, $R^3$, $R^4$, $R^5$, or the ring formed from the joining of $R^1$ and $R^2$, is a hydrophobic moiety.

In certain embodiments, the enhanced NMDA receptor antagonist may comprise one or more hydrophobic moieties. In certain embodiments, the hydrophobic moiety stabilizes molecular conformation of hydrophobic residues GluN1b A74, GluN2B I82, and GluN2B F114 of the NMDA receptor. In yet another embodiment, the hydrophobic moiety physically interacts with the hydrophobic residues, thereby partially or completely antagonizing or inhibiting NMDA receptor function.

In certain embodiments, the hydrophobic moiety may comprise thirteen or more carbon atoms and, optionally, one or more heteroatoms selected from oxygen, nitrogen and sulfur. In certain embodiments, the hydrophobic moiety may comprise twelve or more carbon atoms and one or more halogen atoms, and, optionally, one or more heteroatoms selected from oxygen, nitrogen and sulfur.

In another aspect, provided are pharmaceutical compositions comprising an enhanced NMDA receptor antagonist, e.g., of Formula (I), and optionally a pharmaceutically acceptable excipient. In certain embodiments, the pharmaceutical composition further comprises a second therapeutic agent which is not (is different from) an enhanced NMDA receptor antagonist as described herein. This second therapeutic agent may be a metal ion. In a specific embodiment, the metal ion is zinc.

In yet another aspect, provided is a method of treating an NMDA-mediated disorder, e.g., a neurological disorder, in a subject in need thereof comprising administering to the subject an effective amount of a compound of Formula (I), pharmaceutically acceptable salt thereof, or pharmaceutical composition thereof, as described herein. Exemplary neurological disorders include, but are not limited to, depression, Alzheimer's disease, and Parkinson's disease.

The details of one or more embodiments of the invention are set forth in the accompanying Figures and the Detailed Description. Other features, objects, and advantages of the invention will be apparent from the Examples and from the claims.

DEFINITIONS

Chemical Definitions

Figure 1:
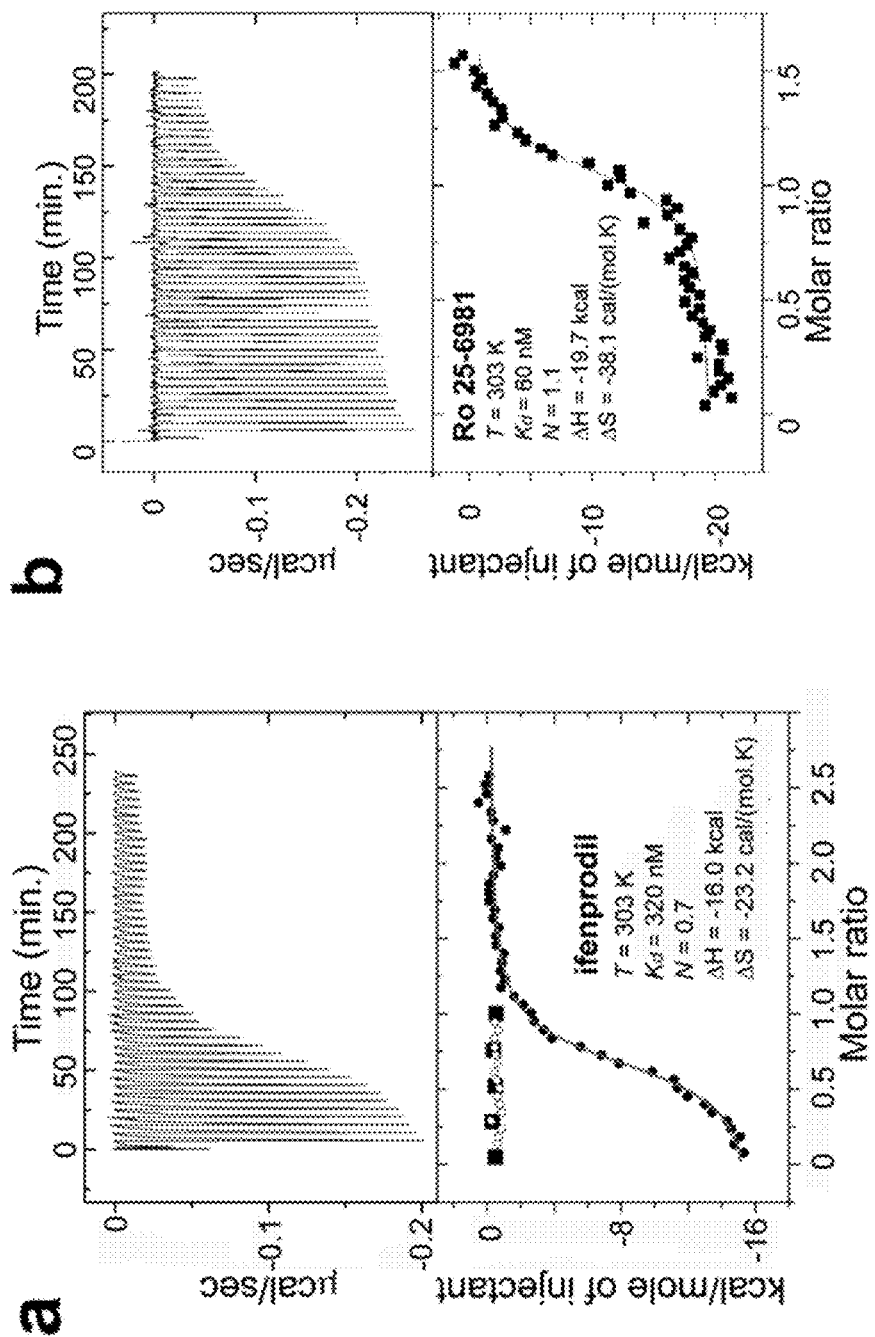
FIG. 1a shows a graph of isothermal titration calorimetry (ITC) analysis of ifenprodil binding to individual or mixed GluN1b ATC and GluN2B ATD proteins.
FIG. 1b shows a graph of ITC analysis of Ro 25-6981 binding to a mixture of GluN1b and GluN2B ATDs using calorimetric titration of Ro 25-6981 into a mixture of GluN1b and GluN2B ATDs.
FIG. 1c shows a graph of a comparison of dependence of weighted-average sedimentation coefficient ($S_w$) values on protein concentration of GluN1b ATD alone, GluN2B ATD alone, and a mixture of GluN1b and GluN2B ATDs in the presence and absence of ifenprodil.
FIG. 1d shows a graph of the sedimentation equilibrium analysis of GluN1b and GluN2B ATDs in the presence of ifenprodil.
FIG. 1e shows a graph of the sedimentation equilibrium analysis of GluN1b and GluN2B ATDs in the absence of ifenprodil.
Figure 1:
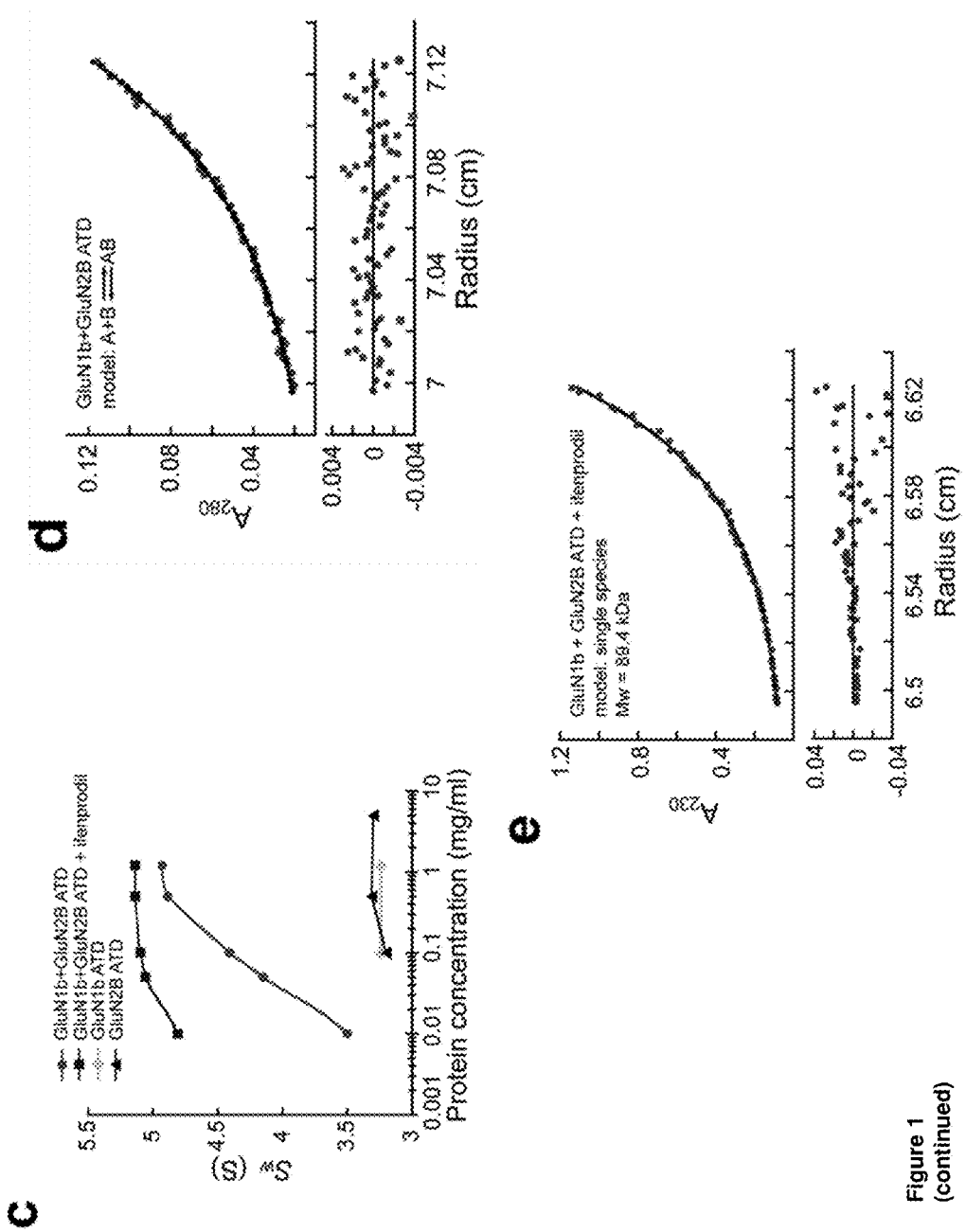

Definitions of specific functional groups and chemical terms are described in more detail below. The chemical elements are identified in accordance with the Periodic Table of the Elements, CAS version, Handbook of Chemistry and Physics, 75th Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5th Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3rd Edition, Cambridge University Press, Cambridge, 1987.

Compounds described herein can comprise one or more asymmetric centers, and thus can exist in various isomeric forms, e.g., enantiomers and/or diastereomers. For example, compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, E. L. *Stereochemistry of Carbon Compounds* (McGraw-Hill, NY, 1962); and Wilen, S. H. *Tables of Resolving Agents and Optical Resolutions* p. 268 (E. L. Eliel, Ed., Univ. of Notre Dame Press, Notre Dame, Ind. 1972). The invention additionally encompasses ligands and complexes as individual isomers substantially free of other isomers, and alternatively, as mixtures of various isomers.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

As used herein, "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an optionally substituted alkyl group is independently unsubstituted (an "unsubstituted alkyl") or substituted (a "substituted alkyl") with one or more substituents. In certain embodiments, the alkyl group is an unsubstituted $C_{1-10}$ alkyl (e.g., —$CH_3$). In certain embodiments, the alkyl group is a substituted $C_{1-10}$ alkyl.

"Perhaloalkyl" is a substituted alkyl group as defined herein wherein all of the hydrogen atoms are independently replaced by a halogen, e.g., fluoro, bromo, chloro, or iodo. In some embodiments, the alkyl moiety has 1 to 8 carbon atoms ("$C_{1-8}$ perhaloalkyl"). In some embodiments, the alkyl moiety has 1 to 6 carbon atoms ("$C_1$ perhaloalkyl"). In some embodiments, the alkyl moiety has 1 to 4 carbon atoms ("$C_1$ perhaloalkyl"). In some embodiments, the alkyl moiety has 1 to 3 carbon atoms ("$C_{1-3}$ perhaloalkyl"). In some embodiments, the alkyl moiety has 1 to 2 carbon atoms ("$C_{1-2}$ perhaloalkyl"). In some embodiments, all of the hydrogen atoms are replaced with fluoro. In some embodiments, all of the hydrogen atoms are replaced with chloro. Examples of perhaloalkyl groups include —$CF_3$, —$CF_2CF_3$, —$CF_2CF_2CF_3$, —$CCl_3$, —$CFCl_2$, —$CF_2Cl$, and the like.

As used herein, "alkenyl" refers to a radical of a straight-chain or branched hydrocarbon group having from 2 to 10 carbon atoms and one or more carbon-carbon double bonds ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an optionally substituted alkenyl group is independently unsubstituted (an "unsubstituted alkenyl") or substituted (a "substituted alkenyl") with one or more substituents. In certain embodiments, the alkenyl group is an unsubstituted $C_{2-10}$ alkenyl. In certain embodiments, the alkenyl group is a substituted $C_{2-10}$ alkenyl.

As used herein, "alkynyl" refers to a radical of a straight-chain or branched hydrocarbon group having from 2 to 10 carbon atoms and one or more carbon-carbon triple bonds ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an optionally substituted alkynyl group is independently unsubstituted (an "unsubstituted alkynyl") or substituted (a "substituted alkynyl") with one or more substituents. In certain embodiments, the alkynyl group is an unsubstituted $C_{2-10}$ alkynyl. In certain embodiments, the alkynyl group is a substituted $C_{2-10}$ alkynyl.

As used herein, "carbocyclyl" refers to a radical of a non-aromatic cyclic hydrocarbon group having from 3 to 10 ring carbon atoms ("$C_{3-10}$ carbocyclyl") and zero heteroatoms in the nonaromatic ring system. In some embodiments, a carbocyclyl group has 3 to 8 ring carbon atoms ("$C_{3-8}$ carbocyclyl"). In some embodiments, a carbocyclyl group has 3 to 6 ring carbon atoms ("$C_{3-6}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of an optionally substituted carbocyclyl group is independently unsubstituted (an "unsubstituted carbocyclyl") or substituted (a "substituted carbocyclyl") with one or more substituents. In certain embodiments, the carbocyclyl group is an unsubstituted $C_{3-10}$ carbocyclyl. In certain embodiments, the carbocyclyl group is a substituted $C_{3-10}$ carbocyclyl.

In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_6$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is an unsubstituted $C_{3-10}$ cycloalkyl. In certain embodiments, the cycloalkyl group is a substituted $C_{3-10}$ cycloalkyl.

As used herein, "heterocyclyl" refers to a radical of a 3- to 14-membered non-aromatic ring system having ring carbon atoms and 1 to 4 ring heteroatoms, wherein each heteroatom is independently selected from nitrogen, oxygen, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of an optionally substituted heterocyclyl is independently unsubstituted (an "unsubstituted heterocyclyl") or substituted (a "substituted heterocyclyl") with one or more substituents. In certain embodiments, the heterocyclyl group is an unsubstituted 3-14 membered heterocyclyl. In certain embodiments, the heterocyclyl group is a substituted 3-14 membered heterocyclyl.

In some embodiments, a heterocyclyl group is a 5-10 membered nonaromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered nonaromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered nonaromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has 1 ring heteroatom selected from nitrogen, oxygen, and sulfur.

Exemplary 3-membered heterocyclyl groups containing 1 heteroatom include, without limitation, azirdinyl, oxiranyl, thiorenyl. Exemplary 4-membered heterocyclyl groups containing 1 heteroatom include, without limitation, azetidinyl, oxetanyl and thietanyl. Exemplary 5-membered heterocyclyl groups containing 1 heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing 2 heteroatoms include, without limitation, dioxolanyl, oxathiolanyl and dithiolanyl. Exemplary 5-membered heterocyclyl groups containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, dioxanyl. Exemplary 6-membered heterocyclyl groups containing 2 heteroatoms include, without limitation, triazinanyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Exemplary 5,5-bicyclic and 5,6-bicyclic heterocyclyl groups include, without limitation, indolinyl, isoindolinyl, dihydrobenzofuranyl, dihydrobenzothienyl, tetra-hydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

As used herein, "aryl" refers to a radical of a monocyclic or polycyclic (e.g., bicyclic or tricyclic) 4n+2 aromatic ring system (e.g., having 6, 10, or 14π electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an optionally substituted aryl group is independently unsubstituted (an "unsubstituted aryl") or substituted (a "substituted aryl") with one or more substituents. In certain embodiments, the aryl group is an unsubstituted $C_{6-14}$ aryl. In certain embodiments, the aryl group is a substituted $C_{6-14}$ aryl.

"Aralkyl" is a subset of "alkyl" and refers to an alkyl group, as defined herein, substituted by an aryl group, as defined herein, wherein the point of attachment is on the alkyl moiety.

As used herein, "heteroaryl" refers to a radical of a 5-14 membered monocyclic or polycyclic (e.g., bicyclic or tricyclic) 4n+2 aromatic ring system (e.g., having 6, 10, or 14π electrons shared in a cyclic array) having ring carbon atoms and 1-4 ring heteroatoms provided in the aromatic ring system, wherein each heteroatom is independently selected from nitrogen, oxygen and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of an optionally substituted heteroaryl group is independently unsubstituted (an "unsubstituted heteroaryl") or substituted (a "substituted heteroaryl") with one or more substituents. In certain embodiments, the heteroaryl group is an unsubstituted 5-14 membered heteroaryl. In certain embodiments, the heteroaryl group is a substituted 5-14 membered heteroaryl.

Exemplary 5-membered heteroaryl groups containing 1 heteroatom include, without limitation, pyrrolyl, furanyl and thiophenyl. Exemplary 5-membered heteroaryl groups containing 2 heteroatoms include, without limitation, imidazolyl, pyrazolyl, oxazolyl, isoxazolyl, thiazolyl, and isothiazolyl. Exemplary 5-membered heteroaryl groups containing 3 heteroatoms include, without limitation, triazolyl, oxadiazolyl, and thiadiazolyl. Exemplary 5-membered heteroaryl groups containing 4 heteroatoms include, without limitation, tetrazolyl. Exemplary 6-membered heteroaryl groups containing 1 heteroatom include, without limitation, pyridinyl. Exemplary 6-membered heteroaryl groups containing 2 heteroatoms include, without limitation, pyridazinyl, pyrimidinyl, and pyrazinyl. Exemplary 6-membered heteroaryl groups containing 3 or 4 heteroatoms include, without limitation, triazinyl and tetrazinyl, respectively. Exemplary 7-membered heteroaryl groups containing 1 heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Exemplary tricyclic heteroaryl groups include, without limitation, phenanthridinyl, dibenzofuranyl, carbazolyl, acridinyl, phenothiazinyl, phenoxazinyl and phenazinyl.

"Heteroaralkyl" is a subset of "alkyl" and refers to an alkyl group, as defined herein, substituted by a heteroaryl group, as defined herein, wherein the point of attachment is on the alkyl moiety.

As used herein, the term "partially unsaturated" refers to a ring moiety that includes at least one double or triple bond. The term "partially unsaturated" is intended to encompass rings having multiple sites of unsaturation, but is not intended to include aromatic groups (e.g., aryl or heteroaryl moieties) as herein defined.

As used herein, a "bond" refers to a single bond, a double bond or a triple bond.

Alkyl, alkenyl, alkynyl, carbocyclyl, heterocyclyl, aryl, and heteroaryl groups, as defined herein, are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom etc.) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$—C(=S)N(R$^{bb}$)$_2$, —C(=O)SR$^{aa}$, —C(=S)SR$^{aa}$, —SC(=S)SR$^{aa}$, —SC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, —P(=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, C$_{3-14}$ carbocyclyl, 3-14 membered heterocyclyl, C$_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NRCO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, OC(=NRf)OR$^{ee}$, —C(=NR$^{ff}$)N(R)$_2$, —OC(=NR$^{ff}$)N(R)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, —P(=O)(R$^{ee}$)$_2$, —OP(=O)(R$^{ee}$)$_2$, —OP(=O)(OR$^{ee}$)$_2$, C$_{1-4}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S;

each instance of R$^{ee}$ is, independently, selected from C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl and 5-10 membered heteroaryl, or two R$^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{gg}$ groups; and each instance of R$^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)$^+$X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-4}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-4}$ alkyl)$_3$, —OSi(C$_{1-6}$ alkyl)$_3$-C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)$_2$(C$_{1-6}$ alkyl), —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, 5-10 membered heteroaryl; or two geminal $R^{gg}$ substituents can be joined to form =O or =S;
wherein $X^-$ is a counterion.

As used herein, the term "hydroxyl" or "hydroxy" refers to the group —OH. The term "substituted hydroxyl" or "substituted hydroxy," by extension, refers to a hydroxyl group wherein the oxygen atom directly attached to the parent molecule is substituted with a group other than hydrogen, and includes groups selected from —OR$^{aa}$, —ON(R$^{bb}$)$_2$, —OC(=O)R$^{aa}$, —OCO$_2$R$^{aa}$, —OC(=O)N(R$^{bb}$)$_2$, —OC(=NR$^{bb}$)R$^{aa}$, —OC(=NR$^{bb}$)OR$^{aa}$, —OC(=NR$^{bb}$)N(R$^{bb}$)$_2$, —OS(=O)R$^{aa}$, —OSO$_2$R$^{aa}$, —OSi(R$^{aa}$)$_3$, —OP(R$^{cc}$)$_2$, —OP(R$^{cc}$)$_3$, —OP(=O)$_2$R$^{aa}$, —OP(=O)(R$^{aa}$)$_2$, —OP(=O)(OR$^{cc}$)$_2$, —OP(=O)$_2$N(R$^{bb}$)$_2$, and —OP(=O)(NR$^{bb}$)$_2$, wherein R$^{aa}$, R$^{bb}$, and R$^{cc}$ are as defined herein.

As used herein, the term "thiol" or "thio" refers to the group —SH. The term "substituted thiol" or "substituted thio," by extension, refers to a thiol group wherein the sulfur atom directly attached to the parent molecule is substituted with a group other than hydrogen, and includes groups selected from —SR$^{aa}$, —S=SR$^{cc}$, —SC(=S)SR$^{aa}$, —SC(=O)SR$^{aa}$, —SC(=O)OR$^{aa}$, and —SC(=O)R$^{aa}$, wherein R$^{aa}$ and R$^{cc}$ are as defined herein.

As used herein, the term, "amino" refers to the group —NH$_2$.

As used herein, the term "primary amino" refers to an amino group wherein the nitrogen atom directly attached to the parent molecule is substituted with one hydrogen and one group other than hydrogen, and includes groups selected from —NH(R$^{bb}$), —NHC(=O)R$^{aa}$, —NHCO$_2$R$^{aa}$, —NHC(=O)N(R$^{bb}$)$_2$, —NHC(=NR$^{bb}$)N(R$^{bb}$)$_2$, —NHSO$_2$R$^{aa}$, —NHP(=O)(OR$^{cc}$)$_2$, and —NHP(=O)(NR$^{bb}$)$_2$, wherein R$^{aa}$, R$^{bb}$ and R$^{cc}$ are as defined herein, and wherein R$^{bb}$ of the group —NH(R$^{bb}$) is not hydrogen.

As used herein, the term "secondary amino" refers to an amino group wherein the nitrogen atom directly attached to the parent molecule is substituted with two groups other than hydrogen, and includes groups selected from —N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —NR$^{bb}$C(=NR$^{bb}$)N(R$^{bb}$)$_2$, —NR$^{bb}$SO$_2$R$^{aa}$, —NR$^{bb}$P(=O)(OR$^{cc}$)$_2$, and —NR$^{bb}$P(=O)(NR$^{bb}$)$_2$, wherein R$^{aa}$, R$^{bb}$, and R$^{cc}$ are as defined herein, with the proviso that the nitrogen atom directly attached to the parent molecule is not substituted with hydrogen.

As used herein, the term "tertiary amino" refers to an amino group wherein the nitrogen atom directly attached to the parent molecule is substituted with three groups, and includes groups selected from —N(R$^{bb}$)$_3$ and —N(R$^{bb}$)$_3$$^+$X$^-$, wherein R$^{bb}$ and X$^-$ are as defined herein.

As used herein, the term "sulfonyl" refers to a group selected from —SO$_2$N(R$^{bb}$)$_2$, —SO$_2$R$^{aa}$, and —SO$_2$OR$^{aa}$, wherein R$^{aa}$ and R$^{bb}$ are as defined herein.

As used herein, the term "sulfinyl" refers to the group —S(=O)R$^{aa}$, wherein R$^{aa}$ is as defined herein.

As used herein, the term "carbonyl" refers a group wherein the carbon directly attached to the parent molecule is sp$^2$ hybridized, and is substituted with an oxygen, nitrogen or sulfur atom, e.g., a group selected from ketones (—C(=O)R$^{aa}$), carboxylic acids (—CO$_2$H), aldehydes (—CHO), esters (—CO$_2$R$^{aa}$, —C(=O)SR$^{aa}$, —C(=S)SR$^{aa}$), amides (—C(=O)N(R$^{bb}$)$_2$, —C(=O)NR$^{bb}$SO$_2$R$^{aa}$, —C(=S)N(R$^{bb}$)$_2$), and imines (—C(=NR$^{bb}$)R$^{aa}$, —C(=NR$^{bb}$)OR$^{aa}$, —C(=NR$^{bb}$)N(R$^{bb}$)$_2$), wherein R$^{aa}$ and R$^{bb}$ are as defined herein As used herein, the term "silyl" refers to the group —Si(R$^{aa}$)$_3$, wherein R$^{aa}$ is as defined herein.

As used herein, the term "boronyl" refers to boranes, boronic acids, boronic esters, borinic acids, and borinic esters, e.g., boronyl groups of the formula —B(R$^{aa}$)$_2$, —B(OR$^{cc}$)$_2$, and —BR$^{aa}$(OR$^{cc}$), wherein R$^{aa}$ and R$^{cc}$ are as defined herein.

As used herein, the term "phosphino" refers to the group —P(R$^{cc}$)$_3$, wherein R$^{cc}$ is as defined herein.

As used herein, the term "halo" or "halogen" refers to fluorine (fluoro, —F), chlorine (chloro, —Cl), bromine (bromo, —Br), or iodine (iodo, —I).

As used herein, a "counterion" is a negatively charged group associated with a positively charged quarternary amine in order to maintain electronic neutrality. Exemplary counterions include halide ions (e.g., F$^-$, Cl$^-$, Br$^-$, I$^-$), NO$_3$$^-$, ClO$_4$$^-$, OH$^-$, H$_2$PO$_4$$^-$, HSO$_4$$^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), and carboxylate ions (e.g., acetate, ethanoate, propanoate, benzoate, glycerate, lactate, tartrate, glycolate, and the like).

Nitrogen atoms can be substituted or unsubstituted as valency permits, and include primary, secondary, tertiary, and quarternary nitrogen atoms. Exemplary nitrogen atom substitutents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups attached to an N atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined above.

In certain embodiments, the substituent present on the nitrogen atom is an amino protecting group. Amino protecting groups include, but are not limited to, —OH, —OR$^{aa}$, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, C(=S)SR$^{cc}$, C$_{10}$ alkyl (e.g., aralkyl, heteroaralkyl), C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined herein. Amino protecting groups are well known in the art and include those described in detail in *Protecting Groups in Organic Synthesis*, T. W. Greene and P. G. M. Wuts, $^{3rd}$ edition, John Wiley & Sons, 1999, incorporated herein by reference.

For example, amino protecting groups such as amide groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxycarbonylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide and o-(benzoyloxymethyl)benzamide.

Amino protecting groups such as carbamate groups (e.g., —C(=O)OR$^{aa}$) include, but are not limited to, methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxycarbonylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, and 2,4,6-trimethylbenzyl carbamate.

Amino protecting groups such as sulfonamide groups (e.g., —S(=O)$_2$R$^{aa}$) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other amino protecting groups include, but are not limited to, phenothiazinyl-(10)-carbonyl derivative, N'-p-toluenesulfonylaminocarbonyl derivative, N'-phenylaminothiocarbonyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N–1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentacarbonylchromium- or tungsten)carbonyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

As used herein, a "hydrophobic moiety" or "hydrophobic substituent" refers to a moiety, or substituent attached thereto, that is non-polar, e.g., that repels a mass of water. Non-polar groups are known in the art. In certain embodiments, the hydrophobic "moiety" is an optionally substituted group comprising 12 or more carbon atoms, e.g., 12, 13, 14, 15, 16, 17, 18, 19, 20, 21, 22, 23, 24, 25, 26, 27 28, 29, or 30 carbon atoms, and optionally, one or more heteroatoms selected from oxygen, nitrogen and sulfur, e.g., 1, 2, 3, or 4 heteroatoms. In certain embodiments, the hydrophobic "moiety" is not substituted with a hydrophilic or polar group, such as, but not limited to, carbonyl, hydroxyl, thiol, amino, primary amino, tertiary amino, boronyl, phosphino, and the like, e.g., groups which may form hydrogen bonds with a hydrogen bond acceptor or hydrogen bond donor. In certain embodiments, the hydrophobic "moiety" is substituted with, for example, halogen, unsubstituted alkyl, unsubstituted alkenyl, unsubstituted alkynyl, unsubstituted aryl, unsubstituted heteroaryl, unsubstituted heterocylyl, or unsubstituted carbocyclyl.

"Ortho", "meta" and "para" is well-understood nomenclature, and describes the location of a substituent on a phenyl ring, or the location of two substituents relative to each other. For example, an "ortho" substituted phenyl describes substitution of a phenyl ring at the 2-position. A "meta" substituted phenyl describes substitution of a phenyl ring at the 3-position. A "para" substituted phenyl describes substitution of a phenyl ring at the 4-position. A phenyl group containing two groups "ortho" to each other describes 2,3-substitution, 3,4-substitution, or 4,5-substitution of the phenyl ring.

These and other exemplary substituents are described in more detail in the Detailed Description, the Examples and in the claims. The invention is not intended to be limited in any manner by the above exemplary listing of substituents.

Other Definitions

As used herein, the term "salt" or "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describes pharmaceutically acceptable salts in detail in *J. Pharmaceutical Sciences* (1977) 66:1-19. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}\text{ alkyl})_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

A "subject" to which administration is contemplated includes, but is not limited to, humans (i.e., a male or female of any age group, e.g., a pediatric subject (e.g, infant, child, adolescent) or adult subject (e.g., young adult, middle-aged adult or senior adult)) and/or other non-human animals, for example mammals (e.g., primates (e.g., cynomolgus monkeys, rhesus monkeys); commercially relevant mammals such as cattle, pigs, horses, sheep, goats, cats, and/or dogs), birds (e.g., commercially relevant birds such as chickens, ducks, geese, and/or turkeys), reptiles, amphibians, and fish. In certain embodiments, the non-human animal is a mammal. The non-human animal may be a male or female and at any stage of development. A non-human animal may be a transgenic animal.

As used herein, "condition" "disorder" and "disease" are used interchangeably.

As used herein, and unless otherwise specified, the terms "treat," "treating" and "treatment" contemplate an action that occurs while a subject is suffering from a specified condition which reduces the severity of the condition or retards or slows the progression of the condition ("therapeutic treatment"), and also contemplates an action that occurs before a subject begins to suffer from the specified condition and which inhibits or reduces the severity of the condition ("prophylactic treatment").

In general, the "effective amount" of a compound refers to an amount sufficient to elicit the desired biological response, i.e., treating or preventing a condition. As will be appreciated by those of ordinary skill in this art, the effective amount of a compound of the invention may vary depending on such factors as the desired biological endpoint, the pharmacokinetics of the compound, the disease being treated, the mode of administration, and the age, health, and condition of the subject. An effective amount encompasses therapeutic as well as prophylactic treatment.

As used herein, and unless otherwise specified, a "therapeutically effective amount" of a compound is an amount sufficient to provide a therapeutic benefit in the therapeutic treatment of a condition or to delay or minimize one or more symptoms associated with the condition. A therapeutically effective amount of a compound means an amount of therapeutic agent, alone or in combination with other therapies, which provides a therapeutic benefit in the therapeutic treatment of the condition. The term "therapeutically effective amount" can encompass an amount that improves overall therapy, reduces or avoids symptoms or causes of the condition, or enhances the therapeutic efficacy of another therapeutic agent.

As used herein, and unless otherwise specified, a "prophylactically effective amount" of a compound is an amount sufficient to prevent the condition, or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

As used herein, use of the phrase "at least one instance" refers to one instance, but also encompasses a range, e.g., for example, from one instance to 4 instances.

DETAILED DESCRIPTION OF CERTAIN EMBODIMENTS OF THE INVENTION

The present invention is directed to enhanced NMDA receptor antagonists, particularly phenylethanolamine-based compounds, which bind NMDA receptors with high affinity and specificity, pharmaceutical compositions thereof, and methods of their use and treatment.

Further disclosed herein is an atomic map of the binding site for enhanced NMDA receptor antagonists, particularly phenylethanolamine-based compounds, within the allosteric domain of the GluN1/GluN2B NMDA receptor, particularly at the interface between GluN1 and GluN2B subunits.

It is the object of the present invention to provide enhanced NMDA receptor antagonists which are phenylethanolamine-based compounds comprising a hydrophobic moiety, which serves to stabilize the molecular conformation of hydrophobic GluN1b and GluN2B residues in the NMDA receptor. As used herein, "stabilize molecular conformation," "stabilize," or "stabilization," refer to the capability of a molecule or moiety to maintain an existing subunit conformation formed by hydrophobic amino acid residues. Stabilization of the NMDA receptor by an enhanced NMDA receptor antagonist described herein may partially or completely inhibit or antagonize NMDA receptor function.

Compounds of the Present Invention

In certain embodiments, the enhanced NMDA receptor antagonist of the present invention is a phenylethanolamine-based compound of Formula (I):

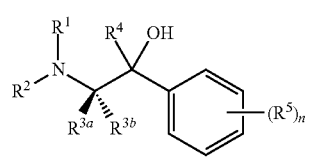

(I)

or a pharmaceutically acceptable salt thereof,
wherein:

$R^1$ and $R^2$ are independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, and an amino protecting group, provided both $R^1$ and $R^2$ are not each hydrogen, or $R^1$ and $R^2$ are joined to form an optionally substituted heterocyclic or optionally substituted heteroaryl ring;

$R^{3a}$, $R^{3b}$, and $R^4$ are independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, and optionally substituted heteroaryl;

each instance of $R^5$ is independently selected from the group consisting of hydroxyl, substituted hydroxyl, thio, substituted thio, amino, primary amino, secondary amino, sulfonyl, sulfinyl, carbonyl, silyl, boronyl, phosphino, halo, optionally substituted alkyl, optionally substituted alkenyl, optionally substituted alkynyl, optionally substituted carbocyclyl, optionally substituted heterocyclyl, optionally substituted aryl, and optionally substituted heteroaryl; and n is 0 or an integer between 1 and 5, inclusive;
provided at least one of $R^1$, $R^2$, $R^3$, $R^4$, $R^5$, or the ring formed from the joining of $R^1$ and $R^2$, is a hydrophobic moiety.

In certain embodiments, the hydrophobic moiety comprises 13 or more carbon atoms, and, optionally, one or more heteroatoms selected from oxygen, nitrogen and sulfur. In certain embodiments, the hydrophobic moiety comprises 12 or more carbon atoms, 1 or more halogen atoms, and, optionally, one or more heteroatoms selected from oxygen, nitrogen and sulfur.

As used herein, the term "enhanced NMDA receptor antagonist" refers to an NMDA receptor antagonist, e.g., of Formula (I), having a greater affinity, greater sensitivity, greater specificity or any combination of these three, as compared to these characteristics of phenylethanolamine-based compounds having NMDA receptor antagonist activity, such as ifenprodil.

Enhanced NMDA receptor antagonists and pharmaceutically acceptable salts thereof antagonize or inhibit, partially or totally, NMDA receptor function. In one embodiment, enhanced NMDA receptor antagonists have an affinity but no efficacy for the NMDA receptor, and binding disrupts the interaction and inhibits the function of an agonist or inverse agonist at receptors. In another embodiment, an enhanced NMDA receptor antagonist mediates its effects by binding to the active site or to allosteric sites on the NMDA receptor, or may interact at a unique binding site not normally involved in the biological regulation of the NMDA receptor activity. In yet another embodiment, enhanced NMDA receptor antagonist activity may be reversible or irreversible, depending on the longevity of the antagonist-receptor complex, which, in turn, depends on the nature of enhanced antagonist receptor binding. In still another embodiment, enhanced NMDA receptor antagonists achieve their potency by competing with endogenous ligands or substrates at structurally-defined binding sites on receptors. The term "antagonize" may refer to blocking, dampening, or inhibiting NMDA receptor function.

In one embodiment, the hydrophobic moiety is a group attached to a N-terminal functional group on the phenylethanolamine-based compound, e.g., the hydrophobic moiety is $R^1$, or $R^2$, or the ring formed from the joining of $R^1$ and $R^2$. In one embodiment, the hydrophobic moiety attached to the phenylethanolamine compound confers the greater affinity and/or greater specificity and/or greater sensitivity of the antagonist to the receptor. The activity of the enhanced or improved NMDA receptor antagonists may have about 10% to about 90%, about 20% to about 80%, 30% to about 70%, 40% to about 60%, or about 50% enhanced NMDA receptor antagonist activity, compared to the activity of ifenprodil. In other aspects, the activity may be about 10%, 15%, 20%, 25%, 30%, 35%, 40%, 45%, 50%, 55%, 60%, 65%, 70%, 75%, 80%, 85%, 90%, or more as compared to the activity of ifenprodil.

As generally defined above, $R^{3a}$, $R^{3b}$, and $R^4$ are independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, and optionally substituted heteroaryl.

In certain embodiments, $R^{3a}$ is hydrogen. In certain embodiments, $R^{3a}$ is optionally substituted alkyl, e.g., $-CH_3$, $-CF_3$, $-CH_2CH_3$, $-CH(CH_3)_2$. In certain embodiments, $R^{3a}$ is optionally substituted alkenyl, e.g., allyl. In certain embodiments, $R^{3a}$ is optionally substituted alkynyl, e.g., propargyl. In certain embodiments, $R^{3a}$ is optionally substituted carbocyclyl, e.g., cyclopropyl. In certain embodiments, $R^{3a}$ is optionally substituted heterocyclyl. In certain embodiments, $R^{3a}$ is optionally substituted aryl. In certain embodiments, $R^{3a}$ is optionally substituted heteroaryl.

In certain embodiments, $R^{3b}$ is hydrogen. In certain embodiments, $R^{3b}$ is optionally substituted alkyl, e.g., $-CH_3$, $-CF_3$, $-CH_2CH_3$, $-CH(CH_3)_2$. In certain embodiments, $R^{3b}$ is optionally substituted alkenyl, e.g., allyl. In certain embodiments, $R^{3b}$ is optionally substituted alkynyl, e.g., propargyl. In certain embodiments, $R^{3b}$ is optionally substituted carbocyclyl, e.g., cyclopropyl. In certain embodiments, $R^{3b}$ is optionally substituted heterocyclyl. In certain embodiments, $R^{3b}$ is optionally substituted aryl. In certain embodiments, $R^{3b}$ is optionally substituted heteroaryl.

In certain embodiments, $R^4$ is hydrogen. In certain embodiments, $R^4$ is optionally substituted alkyl, e.g., $-CH_3$, $-CF_3$, $-CH_2CH_3$, $-CH(CH_3)_2$. In certain embodiments, $R^4$ is optionally substituted alkenyl, e.g., allyl. In certain embodiments, $R^4$ is optionally substituted alkynyl, e.g., propargyl. In certain embodiments, $R^4$ is optionally substituted carbocyclyl, e.g., cyclopropyl. In certain embodiments, $R^4$ is optionally substituted heterocyclyl. In certain embodiments, $R^4$ is optionally substituted aryl. In certain embodiments, $R^4$ is optionally substituted heteroaryl.

In certain embodiments, $R^{3a}$ is hydrogen and $R^{3b}$ is optionally substituted alkyl. In another embodiment, $R^{3b}$ is —$CH_3$. In certain embodiments, $R^{3b}$ is hydrogen and $R^{3a}$ is optionally substituted alkyl. In another embodiment, $R^{3a}$ is —$CH_3$. In certain embodiments, one of $R^{3a}$ and $R^{3b}$ is hydrogen, and one of $R^{3a}$ and $R^{3b}$ is optionally substituted alkyl, e.g., —$CH_3$.

In certain embodiments, $R^4$ is hydrogen.

For example, in certain embodiments wherein $R^4$ is hydrogen, and $R^{3a}$ or $R^{3b}$ is hydrogen, the compound of Formula (I), may be any one of four stereoisomers, e.g., wherein the hydroxyl group —OH is syn or anti to $R^{3a}$ or $R^{3b}$:

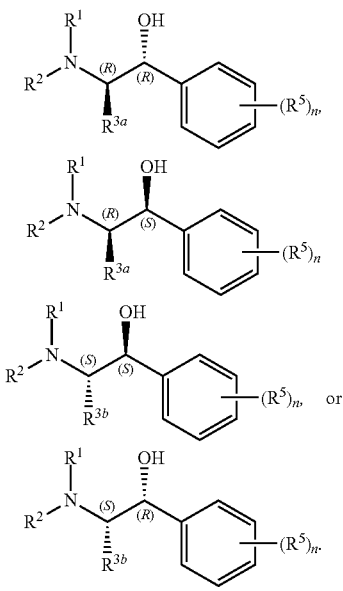

As generally defined above, each instance of $R^5$ is independently selected from the group consisting of hydroxyl, substituted hydroxyl, thio, substituted thio, amino, primary amino, secondary amino, sulfonyl, sulfinyl, carbonyl, silyl, boronyl, phosphino, halo, optionally substituted alkyl, optionally substituted alkenyl, optionally substituted alkynyl, optionally substituted carbocyclyl, optionally substituted heterocyclyl, optionally substituted aryl, and optionally substituted heteroaryl.

In certain embodiments, at least one instance of $R^5$ is hydroxyl. In certain embodiments, at least one instance of $R^5$ is substituted hydroxyl. In certain embodiments, at least one instance of $R^5$ is thio. In certain embodiments, at least one instance of $R^5$ is substituted thio. In certain embodiments, at least one instance of $R^5$ is amino. In certain embodiments, at least one instance of $R^5$ is primary amino. In certain embodiments, at least one instance of $R^5$ is secondary amino. In certain embodiments, at least one instance of $R^5$ is sulfonyl. In certain embodiments, at least one instance of $R^5$ is sulfinyl. In certain embodiments, at least one instance of $R^5$ is carbonyl. In certain embodiments, at least one instance of $R^5$ is silyl. In certain embodiments, at least one instance of $R^5$ is boronyl. In certain embodiments, at least one instance of $R^{5s}$ is phosphine. In certain embodiments, at least one instance of $R^5$ is halo. In certain embodiments, at least one instance of $R^5$ is optionally substituted alkyl. In certain embodiments, at least one instance of $R^5$ is optionally substituted alkenyl. In certain embodiments, at least one instance of $R^s$ is optionally substituted alkynyl. In certain embodiments, at least one instance of $R^5$ is optionally substituted carbocyclyl. In certain embodiments, at least one instance of $R^5$ is optionally substituted heterocyclyl. In certain embodiments, at least one instance of $R^5$ is optionally substituted aryl. In certain embodiments, at least one instance of $R^5$ is optionally substituted heteroaryl.

As generally defined above, n is 0 or an integer between 1 and 5, inclusive;

In certain embodiments, n is 0. In certain embodiments, n is 1. In certain embodiments, n is 2. In certain embodiments, n is 3. In certain embodiments, n is 4. In certain embodiments, n is 5. In certain embodiments, n is 6.

In certain embodiments, n is 1 and $R^5$ is a group provided at the ortho, meta, or para position. In certain embodiments, n is 1 and $R^5$ is hydroxyl provided at the para position.

For example, in certain embodiments of Formula (I) wherein n is 1, $R^5$ is hydroxyl provided at the para position, one of $R^{3a}$ and $R^{3b}$ is hydrogen, and one of $R^{3a}$ and $R^{3b}$ is —$CH_3$, provided is a compound of Formula (I-a):

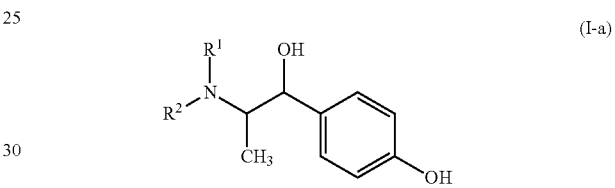

or pharmaceutically acceptable salt thereof, wherein the compound of Formula (I-a) may be any one of four stereoisomers:

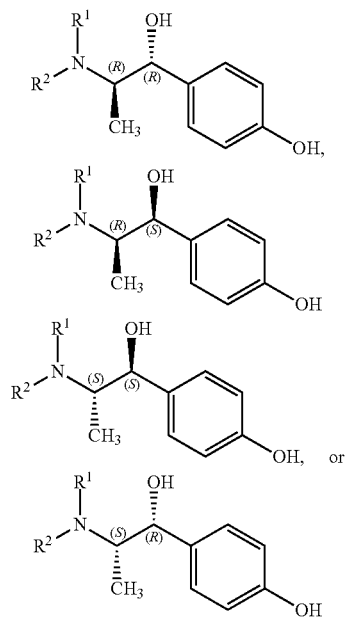

or pharmaceutically acceptable salt thereof, wherein $R^1$ and $R^2$ are as defined herein.

As generally defined above, $R^1$ and $R^2$ are independently selected from the group consisting of hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, and an amino protecting group, provided both $R^1$ and $R^2$ are not each hydrogen, or $R^1$ and $R^2$ are joined to form an optionally substituted heterocyclic or optionally substituted heteroaryl ring.

In certain embodiments, $R^1$ and $R^2$ are joined to form an optionally substituted heterocyclic or optionally substituted heteroaryl ring.

In certain embodiments, $R^1$ and $R^2$ are joined to form an optionally substituted heterocyclic ring, e.g., a 5-6 membered optionally substituted heterocyclyl ring or a 5,6-bicyclic or 6,6-bicyclic optionally substituted heterocyclyl ring. In certain embodiments, $R^1$ and $R^2$ are joined to a 5-6 membered optionally substituted heterocyclyl ring. In certain embodiments, $R^1$ and $R^2$ are joined to a 6-membered optionally substituted heterocyclyl ring, e.g., an optionally substituted piperadinyl or piperazinyl ring. In certain embodiments, $R^1$ and $R^2$ are joined to a 6-membered substituted piperadinyl or substituted piperazinyl ring.

In certain embodiments, the ring formed from the joining of $R^1$ and $R^2$ is of formula:

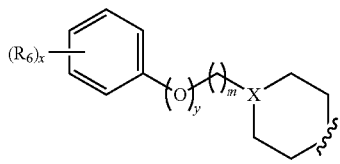

wherein:
X is CH or N;
each instance of $R^6$ is independently selected from the group consisting of substituted hydroxyl, substituted thio, silyl, halo, optionally substituted alkyl, optionally substituted alkenyl, optionally substituted alkynyl, optionally substituted carbocyclyl, optionally substituted heterocyclyl, optionally substituted aryl, and optionally substituted heteroaryl; or two $R^6$ groups ortho to each other are joined to form an optionally substituted carbocyclyl, optionally substituted heterocyclyl, optionally substituted aryl, or optionally substituted heteroaryl group;
x is 0 or an integer between 1 and 5, inclusive;
y is 0 or 1; and
m is 1 or 2.

For example, in certain embodiments of Formula (I), the enhanced NMDA receptor antagonist is of Formula (I-b):

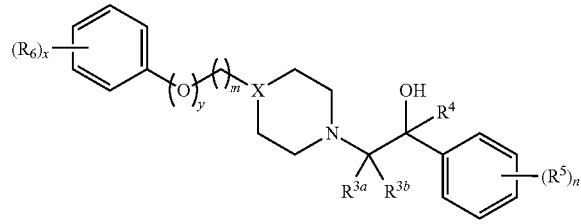

or a pharmaceutically acceptable salt thereof; wherein X, $R^{3a}$, $R^{3b}$, $R^4$, $R^5$, $R^6$, x, n, m, and y are as defined herein.

In certain embodiments, X is CH. In certain embodiments, X is N.

In certain embodiments, m is 1. In certain embodiments, m is 2.

In certain embodiments, y is 0. In certain embodiments, y is 1.

In certain embodiments, m is 1 and y is 0. In certain embodiments, m is 2 and y is 1. In certain embodiments, m is 1 and y is 1. In certain embodiments, m is 2 and y is 0.

In certain embodiments, x is 0. In certain embodiments, x is 1. In certain embodiments, x is 2. In certain embodiments, x is 3. In certain embodiments, x is 4. In certain embodiments, x is 5. In certain embodiments, x is 1 or 2.

In certain embodiments, when x is 2, two $R^6$ groups are ortho to each other. In certain embodiments, when x is 2, two $R^6$ groups ortho to each other are joined to form a ring. In certain embodiments, x is 2, two $R^6$ groups ortho to each other are joined to form an optionally substituted heteroaryl ring.

In certain embodiments, x is 1 and $R^6$ is provided at the para position.

In certain embodiments, each instance of $R^6$ is independently a hydrophobic substituent, as defined herein.

In certain embodiments, each instance of $R^6$ is independently selected from halo, optionally substituted alkyl, optionally substituted carbocyclyl, optionally substituted aryl, or two $R^6$ groups ortho to each other are joined to form a 5-6 membered heteroaryl group.

In certain embodiments, at least one instance of $R^6$ is halo; e.g., —F, —Br, —Cl, or —I.

In certain embodiments, at least one instance of $R^6$ is optionally substituted alkyl, e.g., —$CH_3$, —$CF_3$, —$CH_2CH_3$, —$CF_2CF_3$, —$CH(CH_3)_2$, —$CH_2CH_2CH_3$, —$CH_2CH_2CH_2CH_3$, or —$C(CH_3)_3$.

In certain embodiments, at least one instance of $R^6$ is optionally substituted carbocyclyl, e.g., cyclopropyl, cyclobutyl, cyclopentyl, cyclohexyl.

In certain embodiments, at least one instance of $R^6$ is optionally substituted aryl, e.g., phenyl.

In certain embodiments, two $R^6$ groups ortho to each other are joined to form an optionally substituted 5-membered heteroaryl ring, e.g., an optionally substituted pyrrolyl ring.

In certain embodiments of Formula (I-b), the enhanced NMDA receptor antagonist is of Formula (I-c):

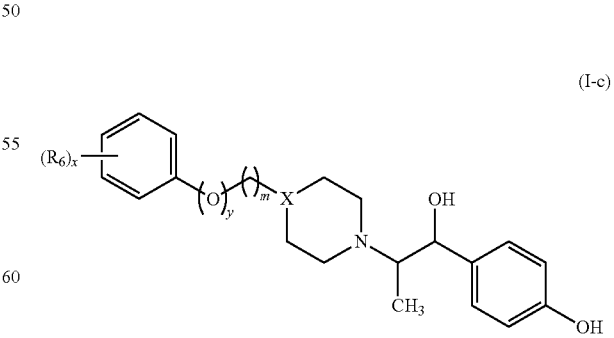

or a pharmaceutically acceptable salt thereof.

In certain embodiments of Formula (I-c), the enhanced NMDA receptor antagonist is of Formula (I-d):

(I-d)

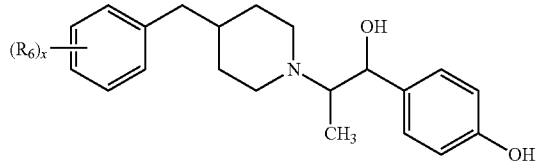

or a pharmaceutically acceptable salt thereof.

In certain embodiments of Formula (I-d), the enhanced NMDA receptor antagonist is of Formula (I-e):

(I-e)

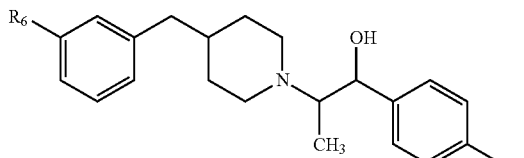

or a pharmaceutically acceptable salt thereof.

In certain embodiments of Formula (I-d), the enhanced NMDA receptor antagonist is of Formula (I-f):

(I-f)

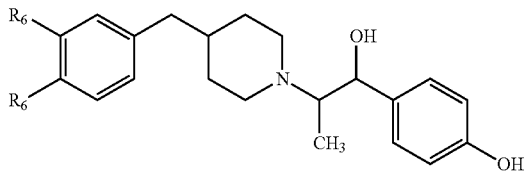

or a pharmaceutically acceptable salt thereof.

In certain embodiments of Formula (I-c), the enhanced NMDA receptor antagonist is of Formula (I-g):

(I-g)

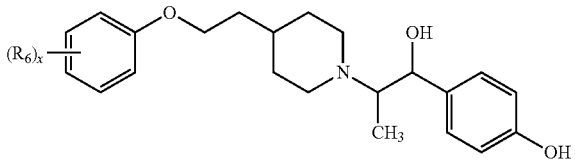

or a pharmaceutically acceptable salt thereof.

In certain embodiments of Formula (I-g), the enhanced NMDA receptor antagonist is of Formula (I-h):

(I-h)

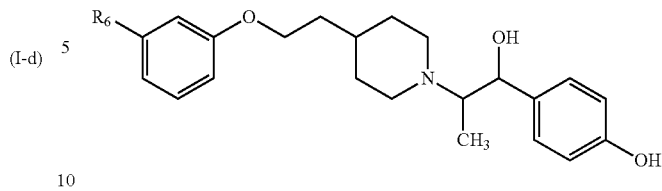

or a pharmaceutically acceptable salt thereof.

In certain embodiments of Formula (I-g), the enhanced NMDA receptor antagonist is of Formula (I-i):

(I-i)

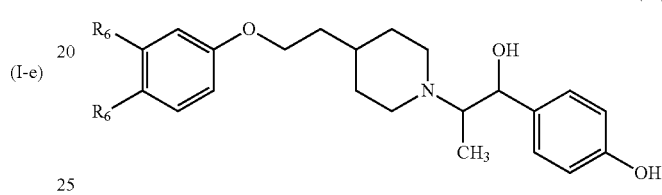

or a pharmaceutically acceptable salt thereof.

In a further another embodiment, the enhanced NMDA receptor antagonist is selected from the group consisting of:

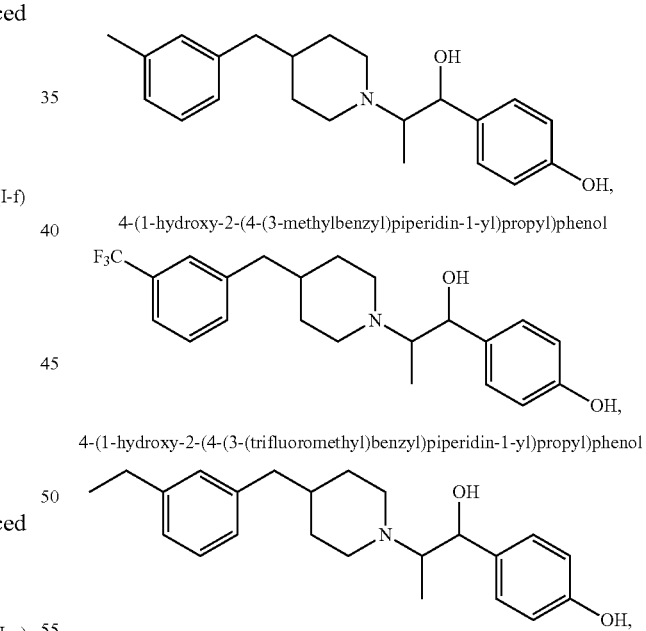

4-(1-hydroxy-2-(4-(3-methylbenzyl)piperidin-1-yl)propyl)phenol 4-(1-hydroxy-2-(4-(3-(trifluoromethyl)benzyl)piperidin-1-yl)propyl)phenol 4-(2-(4-(3-ethylbenzyl)piperidin-1-yl)-1-hydroxypropyl)phenol 4-(1-hydroxy-2-(4-(3-isopropylbenzyl)piperidin-1-yl)propyl)phenol

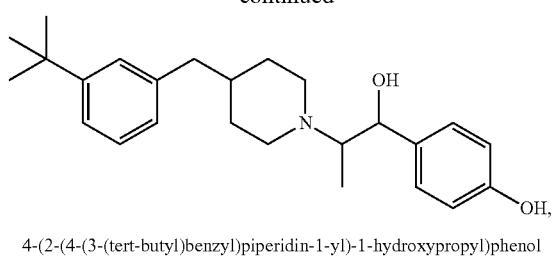

4-(2-(4-(3-(tert-butyl)benzyl)piperidin-1-yl)-1-hydroxypropyl)phenol

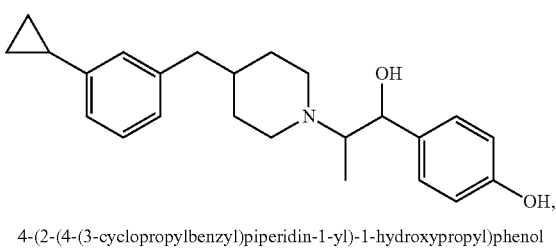

4-(2-(4-(3-cyclopropylbenzyl)piperidin-1-yl)-1-hydroxypropyl)phenol

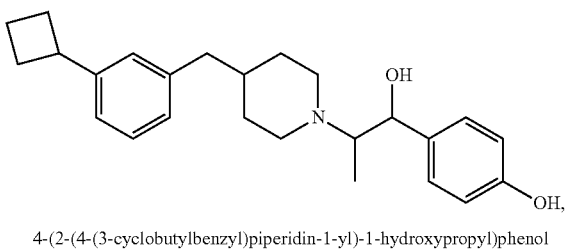

4-(2-(4-(3-cyclobutylbenzyl)piperidin-1-yl)-1-hydroxypropyl)phenol

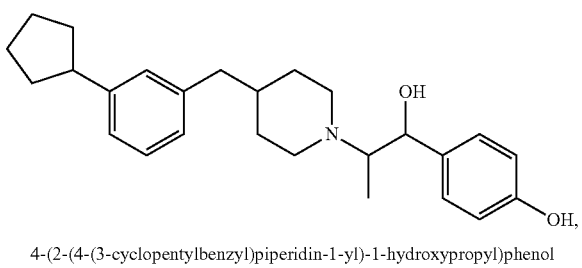

4-(2-(4-(3-cyclopentylbenzyl)piperidin-1-yl)-1-hydroxypropyl)phenol

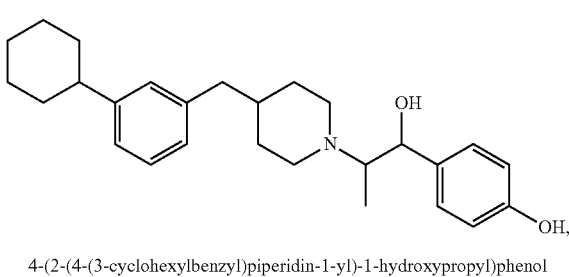

4-(2-(4-(3-cyclohexylbenzyl)piperidin-1-yl)-1-hydroxypropyl)phenol

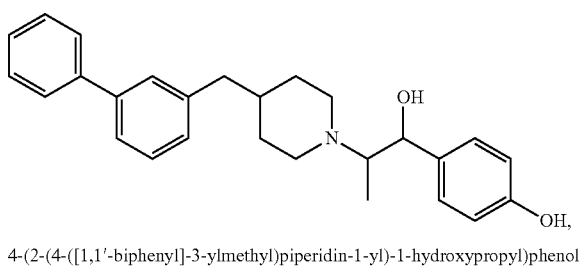

4-(2-(4-([1,1'-biphenyl]-3-ylmethyl)piperidin-1-yl)-1-hydroxypropyl)phenol

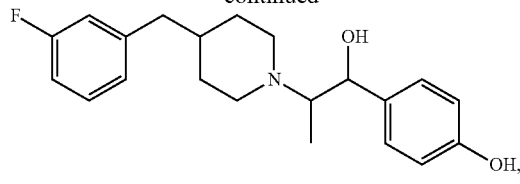

4-(2-(4-(3-fluorobenzyl)piperidin-1-yl)-1-hydroxypropyl)phenol

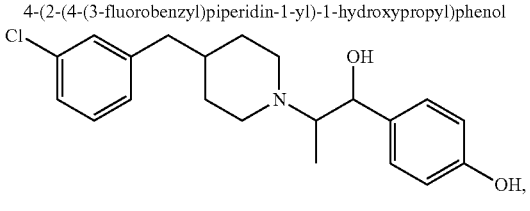

4-(2-(4-(3-chlorobenzyl)piperidin-1-yl)-1-hydroxypropyl)phenol

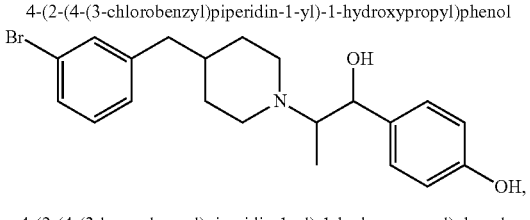

4-(2-(4-(3-bromobenzyl)piperidin-1-yl)-1-hydroxypropyl)phenol

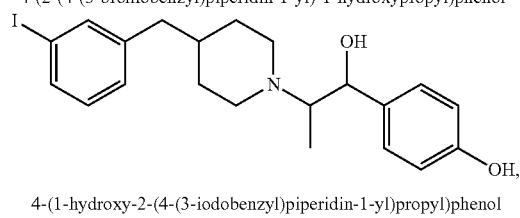

4-(1-hydroxy-2-(4-(3-iodobenzyl)piperidin-1-yl)propyl)phenol

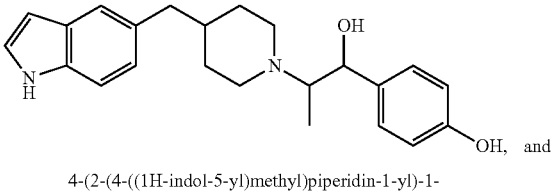

4-(2-(4-((1H-indol-5-yl)methyl)piperidin-1-yl)-1-hydroxypropyl)phenol, and

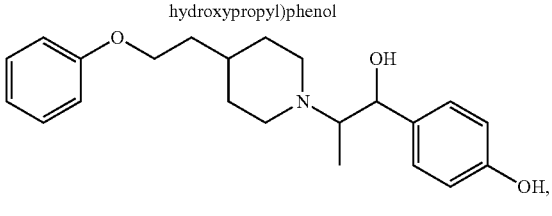

4-(1-hydroxy-2-(4-(2-phenoxyethyl)piperidin-1-yl)propyl)phenol and pharmaceutically acceptable salts thereof.

Pharmaceutical Compositions and Formulations

The present invention further provides pharmaceutical compositions comprising an enhanced NMDA receptor antagonist, e.g., a compound of Formula (I), or pharmaceutically acceptable salt thereof, and optionally a pharmaceutically acceptable excipient. In certain embodiments, the enhanced NMDA receptor antagonist is provided in an effective amount in the pharmaceutical composition.

Pharmaceutically acceptable excipients include any and all solvents, diluents or other liquid vehicles, dispersion or suspension aids, surface active agents, isotonic agents, thickening or emulsifying agents, preservatives, solid binders, lubricants and the like, as suited to the particular dosage form desired. General considerations in formulation and/or manufacture of pharmaceutical compositions agents can be found, for example, in *Remington's Pharmaceutical Sciences*, Sixteenth Edition, E. W. Martin (Mack Publishing Co., Easton, Pa., 1980), and *Remington: The Science and Practice of Pharmacy*, 21st Edition (Lippincott Williams & Wilkins, 2005).

Pharmaceutical compositions described herein can be prepared by any method known in the art of pharmacology. In general, such preparatory methods include the steps of bringing the compound of the present invention (the "active ingredient") into association with a carrier and/or one or more other accessory ingredients, and then, if necessary and/or desirable, shaping and/or packaging the product into a desired single- or multi-dose unit.

Pharmaceutical compositions can be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition of the invention will vary, depending upon the identity, size, and/or condition of the subject treated and further depending upon the route by which the composition is to be administered. An enhanced NMDA receptor antagonist may be administered orally, topically, parenterally, with inhalation or spray, sublingually, transdermally, rectally, in the form of an eye ointment or by other methods, in the standard dosage forms containing conventional nontoxic pharmaceutically acceptable carriers, adjuvants and media. The one or more excipients should be sufficiently pure and sufficiently low-toxic so as to regard them appropriate for the administration to an animal being treated. A carrier may be inert or may have its own pharmaceutically favorable properties. An amount of the carrier used in combination with the compound is sufficient to provide practical quality of the material to be administered per unit dose of the compound.

Enhanced NMDA receptor antagonists provided herein are typically formulated in dosage unit form for ease of administration and uniformity of dosage. It will be understood, however, that the total daily usage of the compositions of the present invention will be decided by the attending physician within the scope of sound medical judgment. The specific therapeutically effective dose level for any particular subject will depend upon a variety of factors including the disorder being treated and the severity of the disorder; the activity of the specific active ingredient employed; the specific composition employed; the age, body weight, general health, sex and diet of the subject; the time of administration, route of administration, and rate of excretion of the specific active ingredient employed; the duration of the treatment; drugs used in combination or coincidental with the specific active ingredient employed; and like factors well known in the medical arts.

The exact amount of the enhanced NMDA receptor antagonist required to achieve an effective amount will vary from subject to subject, depending, for example, on species, age, and general condition of a subject, severity of the side effects or disorder, identity of the particular compound(s), mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

In certain embodiments, an effective amount of an enhanced NMDA receptor antagonist for administration one or more times a day to a 70 kg adult human may comprise about 0.0001 mg to about 3000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 10 mg to about 1000 mg, or about 100 mg to about 1000 mg, of a compound per unit dosage form.

It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

Examples of pharmaceutically acceptable excipients are sugars, such as lactose, glucose and saccharose; starches, such as corn starch and potato starch; cellulose and derivatives thereof, such as sodium carboxymethylcellulose, ethylcellulose and methylcellulose; powdered tragacanth gum; gelatine; talc; solid lubricants such as stearinic acid and magnesium stearate; calcium sulfate, vegetable oils, such as peanut butter, cottonseed oil and corn oil; polyols, such as propylene glycol, glycerin, sorbitol, mannitol and polyethylene glycol; alginic acid; emulsifiers, such as tweens; wetting agents, such as sodium laurylsulfate; dyes; correctives; pelletizing agents; stabilizers; antioxidants; preservatives; pyrogen-free water; isotonic physiological solution, glucose solution and phosphate-buffered solutions.

In particular, pharmaceutically acceptable excipients for systemic administration comprise sugars, starches, cellulose and derivative thereof, malt, gelatin, talc, calcium sulfate, vegetable oils, synthetic oils, polyols, alginic acid, phosphate-buffered solutions, emulsifiers, isotonic physiological solution and pyrogen-free water. Carriers for parenteral administration are propylene glycol, ethyl oleate, pyrrolidone, ethanol and oil.

Optional active agents that do not significantly affect the activity of an enhanced NMDA receptor antagonist described herein may be added to the pharmaceutical composition.

One or more enhanced NMDA receptor antagonist described herein are mixed at effective concentrations with an appropriate pharmaceutical carrier(s), excipients, an adjuvant or a medium. If the one or more enhanced NMDA receptor antagonist is not sufficiently soluble, solubilization methods may be used. Such methods are known to those of skill in the art and can make use of co-solvents, such as dimethylsulfoxide (DMSO), and/or of surfactants, such as tween, or dissolving the one or more enhanced NMDA receptor antagonist in an aqueous solution of sodium bicarbonate and other methods.

After admixing or combining the one or more enhanced NMDA receptor antagonists, the resulting mixture may be a solution, suspension, emulsion, or a similar preparation. The form of the mixture will vary, depending on considerations such as the prospective route of administration and solubility of the one or more enhanced NMDA receptor antagonists in the chosen carrier or medium. The effective concentration sufficient to relieve the symptoms of a disease, disorder or condition which is being treated may be determined empirically.

The pharmaceutical compositions comprising the enhanced NMDA receptor antagonists described herein may be in the form suitable for oral administration, for example, in the forms of tablets or granules, pastilles, troches, suspensions in water or oil, dispersible powders or granules, emulsions, hard or soft capsules, or syrups or elixirs. The compositions intended for oral administration may be prepared according to any method known in the art for the preparation of pharmaceutical compositions, and these compositions may contain one or more agents, such as sweeteners, correctives, flavoring agents, dyes and preservatives, useful to produce compositions attractive in appearance and pleasant for ingestion.

Oral preparations contain 0.1 to 99% of the one or more enhanced NMDA receptor antagonists and, typically, at least about 20% (% by weight) of the compound of the present invention. Some embodiments contain about 25% to about 50% or 5% to 75% of the one or more enhanced NMDA receptor antagonists.

Enhanced NMDA receptor antagonists may be formulated into liquid preparations for oral administration, such as suspensions in water or oil, solutions, emulsions, syrups or elixirs, for example. A preparation comprising one or more enhanced NMDA receptor antagonist may be a dry product which is mixed with water or other appropriate medium before use. These liquid preparations may comprise conventional additives, such as suspending agents (for example, a sorbitol syrup, methylcellulose, glucose/sugar, syrup, gelatin, hydroxyethylcellulose, carboxymethylcellulose, aluminum stearate gel and hydrogenated edible fats), emulsifiers (for example, lecithin, sorbitan monostearate or Arabic gum), non-aqueous media which can comprise edible oils (for example, almond oil, fractionated coconut oil, silyl ethers, propylene glycol and ethyl alcohol), and preservatives (for example, methyl- or n-propyl-p-hydroxy benzoate and sorbic acid).

The compositions administered orally also may comprise liquid solutions, emulsions, suspensions, powders, granules, elixirs, tinctures, syrups and the like forms. The pharmaceutically acceptable carriers suitable for the preparation of such compositions are well-known in the art. Oral compositions may comprise preservatives, correctives, sweeteners, such as sucrose or saccharine, flavor hiding agents, and dyes.

The typical components of carriers for syrups, elixirs, emulsions and suspensions are ethanol, glycerin, propylene glycol, polyethylene glycol, sugar solution, sorbitol and water. Syrups and elixirs may comprise sweeteners, for example, glycerin, propylene glycol, sorbitol or saccharose. Such compositions may also contain a demulcent.

In the case of a suspension, typical suspending agents are methylcellulose, carboxymethylcellulose sodium, avicel RC-591, tragacanth and sodium alginate; typical wetting agents are lecithin and polysorbate 80; and typical preservatives are methyl paraben and sodium benzoate.

Aqueous suspensions may comprise the active agent(s) in a mixture with excipients suitable for obtaining aqueous suspensions. These excipients may be suspending agents, for example, carboxymethylcellulose sodium, methylcellulose, hydropropylmethyl cellulose, sodium alginate, polyvinyl pyrrolidone, tragacanth gum and Arabic gum; dispersing or wetting agents; naturally-occurring phosphatides, for example, lecithin, or products of condensation of alkylenoxide with fatty acids, for example, polyoxyethylene stearate, or products of condensation of ethylene oxide with long-chain aliphatic alcohols, for example, with heptadecaethylene oxycetanol, or products of condensation of ethylene oxide with partial esters produced from fatty acids and hexitol, such as substituted polyoxyethylene sorbitol, or products of condensation of ethylene oxide with partial esters produced from fatty acids and hexitol anhydrides, for example, substituted polyoxyethylene sorbitan. Aqueous suspensions may also contain some preservatives, for example ethyl- or n-propyl-p-hydroxybenzoate.

Oil suspensions may be prepared by suspending active ingredients in a vegetable oil, such as peanut butter, olive oil, sesame oil and coconut oil, or in a mineral oil, such as liquid paraffin. Oil suspension may contain a thickening agent, for example, bee wax, solid paraffin or cetyl alcohol. Some sweeteners, such as mentioned above, and correctives can be added to obtain pleasant oral preparations. These compositions may be preserved by adding an anti-oxidant, such as ascorbic acid.

The pharmaceutical compositions may also be in the form of oil-in-water emulsions. The oil phase may be a vegetable oil, such as olive oil or peanut butter, or a mineral oil, for example, liquid paraffin or mixtures thereof. The appropriate emulsifiers may be naturally occurring gums, for example, Arabic gum or tragacanth gum, naturally occurring phosphatides, for example, soybean lecithin, and esters or partial esters produced from fatty acids and hexitol anhydrides, for example, sorbitan monooleate, and products of condensation of said partial esters with ethylene oxide, for example, polyoxyethylene sorbitan monooleate.

Dispersing powders and granules suitable for preparing an aqueous suspension by adding water are the active ingredient in a mixture with a dispersing or wetting agent, suspending agent and one or more preservatives. The appropriate dispersing or wetting agents and suspending agents are the agents already exemplified above.

Tablets typically contain conventional pharmaceutically compatible auxiliary agents such as inert diluents, such as calcium carbonate, sodium carbonate, mannitol, lactose and cellulose; binders, such as starch, gelatin and saccharose; dispersing agents, such as starch, alginic acid and croscarmellose; lubricants such as magnesium stearate, stearic acid and talc. Glidants, such as silicon dioxide may be used to improve fluidity characteristics of a powder composition. For appearance, dyes such as FD&C may be added. Sweeteners and correctives such as aspartame, saccharine, menthol, peppermint and fruit flavors are useful as adjuvants for chewable tablets. Capsules (including sustained release and delayed release preparations) typically contain one or more solid diluents described above. The selection of carrier components often depends on secondary factors such as flavor, price and storage stability.

These compositions may also be coated using conventional methods, typically with a pH-dependent coating, so that the desired compound is released in the gastro-intestinal tract in the proximity to the desired administration site or at different time points to sustain the desired effect. Such dosage forms typically comprise one or more components from among cellulose acetate phthalate, polyvinyl acetate phthalate, hydroxypropylmethylcellulose phthalate, ethyl cellulose, Eudragit coatings, waxes and shellac and other materials.

Preparations for oral administration may be formulated into hard gelatin capsules. The one or more enhanced NMDA receptor antagonists are mixed with an inert solid diluent, such as calcium carbonate, calcium phosphate and kaolin, or in the form of soft gelatin capsules, in which case the one or more enhanced NMDA receptor antagonists are mixed with water or an oil medium, such as peanut butter, liquid paraffin or olive oil.

Pharmaceutical compositions may be in the form of a sterile water or oil suspension for injections. Such suspension may be prepared according to the prior art using appropriate dispersing or wetting agents and suspending agents mentioned above. A sterile preparation for injections may also be a sterile solution for injections or a suspension for injections in a non-toxic parenterally acceptable diluent or solvent, for example, in the form of a solution in 1,3-butandiol. Among acceptable media and solvents, which may be used, are water, Ringer solution and an isotonic sodium chloride solution. Moreover, sterile nonvolatile oils are usually used as a solvent or a suspending medium. For this purpose, any mixture of nonvolatile oils may be used including mono- and diglycerides. Moreover, for obtaining preparations for injections, fatty acids such as oleinic acid may be applicable.

The enhanced NMDA receptor antagonist may be administered parenterally in a sterile medium. The parenteral administration may comprise hypodermic injections, intravenous, intramuscular and intrathecal injections or infusion methods. A medicinal agent, depending on the medium and concentrations used, may be either suspended or dissolved in the medium. Dissolving in a medium of adjuvants, such as local anesthetics, preservatives and buffering agents may be advantageous. In the compositions for parenteral administration a carrier amounts to at least around 90% by weight of the total composition.

Enhanced NMDA receptor antagonists may also be administered in the form of suppositories for rectal or vaginal administration of a medicinal agent. Such compositions may be prepared by mixing the medicinal agent with an appropriate non-irritating excipient which is solid at ordinary temperatures, but liquid at rectal temperature and will, consequently, melt in the rectum releasing a medicinal agent. These agents are cocoa oil and polyethylene glycols.

Alternatively, enhanced NMDA receptor antagonists may be formulated into a composition for local or topical application, for example, for topical application on skin or mucous membranes such as eyes, in the form of gels, creams and lotions for application to eyes or for intracisternal or intraspinal application. Topical compositions of the present inventions may be in any form including, for example, in the form of solutions, creams, ointments, gels, lotions, milk, cleansing refreshers, wetting agents, sprays, dermal patches and the likes.

Such solutions may be prepared with appropriate salts in the form of 0.01%-10% isotonic solutions, pH is about 5-7. Enhanced NMDA receptor antagonists may also be formulated into a composition for transdermal administration in the form of transdermal patches.

The compositions for topical application comprising one or more enhanced NMDA receptor antagonist may be mixed with different carrier materials well known in the art such as, for example, water, alcohols, aloe vera gel, allantoin, glycerin, oils with vitamins A and E, a mineral oil, propylene glycol PPG-2, myristyl propionate and the like.

Other materials for application in the carriers for topical compositions are, for example, emollients, solvents, wetting agents, thickeners and powders. Examples of each of the material types which may be used separately or mixed with one or more materials are the following agents: emollients—stearyl alcohol, glycerol monoricinoleate, glyceryl monostearate, propan-1,2-diol, butan-1,3-diol, mink fat, cetyl alcohol, isopropyl isostearate, stearic acid, isobutyl palmitate, isocetyl stearate, oleyl alcohol, isopropyl laurate, hexyl laurate, decyl oleate, octadecane-2-ol, isocetyl alcohol, cetyl palmitate, dimethylpolysiloxane, di-n-butylsebacate, isopropyl myristate, isopropyl palmitate, isopropyl stearate, butyl stearate, polyethylene glycol, triethylene glycol, lanolin, sesame oil, coconut oil, peanut butter, castor oil, acetylated lanolin alcohols, vaseline, mineral oil, butyl myristate, isostearic acid, palmitic acid, isopropyl linoleate, lauryl lactate, myristyl lactate, decyl oleate and myristyl myristate; propellants—propane, butane, isobutane, dimethyl ether, carbon dioxide and nitrogen oxide; solvents—ethyl alcohol, methylene chloride, isopropanol, castor oil, ethylene glycol monoethyl ester, diethylene glycol monobutyl ester, diethylene glycol monoethyl ester, dimethyl sulfoxide, dimethyl formamide, tetrahydrofuran; wetting agents—glycerol, sorbitol, sodium 1-pyrrolidone-5-carboxylate, soluble collagen, dibutyl phthalate and gelatin; and powders, such as chalk, talc, Fuller's earth, kaolin, starch, gums, colloidal silicon dioxide, sodium polyacrylate, tetraalkylammonium smectites, trialkylarylammonium smectites, chemically modified magnesium aluminum silicate, organically modified montmorrilonite clay, hydrated aluminum silicate, finely dispersed silicon dioxide, carboxyvinyl polymer, carboxymethylcellulose sodium and ethylene glycol monostearate.

Enhanced NMDA receptor antagonists may also be administered topically in the form of liposomal delivery systems such as small single layer vesicles, large single layer vesicles and multi-layered vesicles. Liposomes may be produced from a range of phospholipids, such as cholesterol, stearyl amine or phosphatidylcholines.

Other compositions useful for systemic delivery of the enhanced NMDA receptor antagonists comprise sublingual and nasal dosage forms. Such compositions typically contain one or more fillers such as saccharose, sorbitol and mannitol, and binders such as Arabic gum, microcrystal cellulose, carboxymethylcellulose and hydroxypropylmethylcellulose. Glidants, lubricants, sweeteners, dyes, antioxidants and correctives described above can also be incorporated.

The compositions for inhalation typically may be formulated in a solution, suspension or emulsion, which may be administered in the form of a dry powder or in the form of an aerosol using a conventional propellent (for example, dichlorodifluoromethane and tri chloro fluoromethane).

In certain embodiments, the pharmaceutically acceptable excipient is selected from the group consisting of water, buffer, an organic solvent, a pharmaceutically acceptable oil or fat, or a combination thereof. In certain embodiments, the pharmaceutical composition further comprises a pharmaceutical additive, for example, solubilizer, emulsifier, preservative, sweetener, flavoring agent, suspending agent, thickening agent, color, viscosity regulator, stabilizer, osmo-regulator, or a combination of any two or more thereof.

Methods of Use and Treatment

The present invention further provides methods of using enhanced NMDA receptor antagonists as described herein. For example, in one aspect, provided are methods of treating an NMDA-mediated disorder, comprising administering to a subject in need thereof an effective amount of an enhanced NMDA receptor antagonist, e.g., a compound of Formula (I) or a pharmaceutically acceptable salt thereof, or pharmaceutical composition thereof.

Exemplary NMDA-mediated disorders include, but are not limited to, neuropathies and neurological disorders, including, but not limited to, depression, peripheral neuropathies (e.g., such as traumatic (nerve severing or crushing), ischemic, metabolic (diabetes, uraemia), infectious, alcoholic, iatrogenic, or genetic neuropathies), diseases involving motor neurons (e.g., such as spinal amyotrophies and amyotrophic lateral sclerosis), and chronic neurodegenerative diseases involving a degeneration of central nervous system axons (e.g., such as Alzheimer's disease, Parkinson's disease, and multiple sclerosis). In certain embodiments, the NMDA-mediated disorder is a neurological disorder. In certain embodiments, the neurological disorder is depression, Alzheimer's disease, or Parkinson's disease.

It will be also appreciated that an enhanced NMDA receptor antagonist or composition thereof, as described herein, can be administered in combination with one or more additional therapeutically active agents, e.g., one or more additional therapeutically active agents that improve bioavailability, reduce and/or modify metabolism, inhibit excretion, and/or modify distribution within the body. It will also be appreciated that the therapy employed may achieve a desired effect for the same disorder, and/or it may achieve different effects.

The enhanced NMDA receptor antagonist can be administered concurrently with, prior to, or subsequent to, one or more additional therapeutically active agents. In general, each agent will be administered at a dose and/or on a time schedule determined for that agent. In will further be appreciated that the additional therapeutically active agent utilized in this combination can be administered together in a single composition or administered separately in different compositions. The particular combination to employ in a regimen will take into account compatibility of the enhanced NMDA receptor antagonist with the additional therapeutically active agent and/or the desired therapeutic effect to be achieved. In general, it is expected that additional therapeutically active agents utilized in combination be utilized at levels that do not exceed the levels at which they are utilized individually. In some embodiments, the levels utilized in combination will be lower than those utilized individually.

Exemplary additional therapeutically active agents include, but are not limited to, metals/metal ions, anesthetics, steroidal agents, steroidal or non-steroidal anti-inflammatory agents, immunosuppressant agents, antigens, sedatives, opioids, pain-relieving agents, analgesics, hormones, and prostaglandins, etc. Therapeutically active agents include small organic molecules such as drug compounds (e.g., compounds approved by the US Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins and cells.

In certain embodiments, the additional therapeutically active agent has NMDA receptor antagonist activity.

In certain embodiments, the additional therapeutically active agent is a metal or metal ion. In a specific embodiment, the metal or metal ion is elemental zinc or a zinc ion.

In Silico Methods

The present invention further provides in silico methods of designing enhanced NMDA receptor antagonists, e.g., of Formula (I), using, for example, the three-dimensional X-ray coordinates of the heterodimers GluN1 and GluN2B subunits obtained when bound to ifenprodil. X-ray coordinates are available from the RCSB Protein Data Bank (PDB) (www.rcsb.org) using accession codes 3QEK for GluN1bATD, 3QEL for GluN1b-GluN2B ATD in complex with ifenprodil, and 3QEM for GluN1b-GluN2B ATD in complex with Ro 25-698. Each set of X-ray coordinates for each of these complexes is incorporated herein by reference in its entirety. See also Karakas, Simorowski and Furukawa, *Nature Letter* (2011) 475:249-253, and accompanying Supplementary Information, the entirety of each of which is incorporated herein by reference.

The atomic coordinates of the heterodimers GluN1 and GluN2B subunits complexed with ifenprodil or Ro 25-6981, e.g., the atomic coordinates of the binding pocket, can be used to computationally screen for small molecules that bind to in order to select, design, and/or develop compounds that bind to the heterodimers GluN1 and GluN2B subunits with a higher affinity than ifenprodil. Those of skill in the art may identify inhibitors as competitive, uncompetitive or non-competitive or reversible inhibitors by computer fitting enzyme kinetic data using standard equations according to, for example, *Enzyme Kinetics* by Segel (1975) J. Wiley & Sons, incorporated herein by reference, or by employing assays which measure the ability of a potential enhanced NMDA inhibitor.

In one aspect, provided is an in silico method of identifying a candidate enhanced NMDA receptor antagonist which binds within the allosteric domain of the GluN1/GluN2B NMDA receptor comprising the steps of: (a) using a three-dimensional structure of GluN1 and GluN2B bound to ifenprodil to model the complex in silico; (b) replacing the ifenprodil of the complex as determined in step (a) with structure coordinates for other candidate ligand(s); (c) selecting (e.g., synthesizing and/or choosing) those candidate ligands from step (b) which fit into the binding site of GluN1/GluN2B; and optionally (d) contacting the potential ligands identified in step (c) in an in vitro or in vivo assay with GluN1/GluN2B to determine which candidate ligands bind to GluN1/GluN2B thereby identifying new candidate ligands.

In certain embodiments, the method further comprises modifying the candidate ligand to alter, add or eliminate a portion thereof suspected of interacting with a binding site of the binding cavity thereby increasing the affinity of the ligand to the binding site or binding cavity. Synthesis and synthetic modification of compounds contemplated herein, e.g., of Formula (I), may follow synthetic procedures well known in the art. See, for example, Mercer et al., *Journal of Neurochemistry* (1993) 61:120-126; Chenard et al., *J. Med. Chem.* (1991) 34:3085-3090. See also Example 6, below.

Suitable computer programs which may be used in the design and selection of potential binding compounds (e.g., by selecting suitable chemical fragments) include, but are not limited to, GRID (Goodford (1985) *J. Med. Chem.* 28:849 857); MCSS (Miranker, A. and M. Karplus, (1991) *Proteins: Structure. Function and Genetics,* 11:29-34); AUTODOCK (Goodsell, D. S, and A. J. Olsen (1990) *Proteins: Structure. Function, and Genetics* 8:195 202); and DOCK (Kuntz et al. (1982) *J. Mol. Biol.* 161:269-288), each of which is incorporated herein by reference.

Suitable computer programs which may be used in connecting the individual chemical entities or fragments include, but are not limited to, CAVEAT (Bartlett, (1989) *Molecular Recognition in Chemical and Biological Problems*, Special Pub., Royal Chem. Soc. 78:182-196); and 3*D Database systems such as MACCS*-3*D* by MDL Information Systems, San Leandro, Calif.), HOOK (Molecular Simulations, Burlington, Mass.) and as reviewed in Martin, Y. C., (1992) *J. Med. Chem.* 35:2145 2154), each of which is hereby incorporated herein by reference.

In addition to the method of building or identifying a potential binding compound in a step-wise fashion (e.g., one fragment or chemical entity at a time as described above), potential binding compounds may be designed as a whole or "de novo" using either an empty active site or, optionally, including some portion of a known inhibitor, activator or binding compound. Suitable computer programs include, but are not limited to, LUDI (Bohm, (1992) *J. Comp. Aid. Molec. Design* 6:61-78); LEGEND (Nishibata, Y. and A. Itai, (1991) *Tetrahedron* 47:8985); and LEAPFROG (Tripos Associates, St. Louis, Mo.). Other molecular modeling techniques may also be employed in accordance with this invention; see, for example, Cohen, N. C. et al. (1990) *J. Med. Chem.* 33: 883-

894, and Navia (1992) *Current Opinions in Structural Biology* 2:202-210; each of which is hereby incorporated herein by reference.

Once a binding compound has been designed, selected, identified, synthesized, or chosen by the methods described herein, the affinity with which that compound binds to GluN1 and GluN2B may be tested by computational or biochemical evaluation. A compound designed, or selected, or synthesized, or chosen as a binding compound may be further computationally optimized so that in its bound state it would preferably lack repulsive interactions with the target site. Such non-complementary (e.g., electrostatic) interactions include repulsive charge-charge, dipole-dipole, and charge-dipole interactions. Specifically, the sum of all electrostatic interactions between the potential binding compound and the site at which it is bound to GluN1 and GluN2B, in certain embodiments, make a neutral or favorable contribution to the enthalpy of binding. Suitable computer software which may be used to evaluate compound deformation energy and electrostatic interactions, includes, but is not limited to, Gaussian 92, revision C by M. J. Frisch, Gaussian, Inc., (1992) Pittsburgh, Pa.; *AMBER*, version 4.0 by P. A. Kollman, (1994) University of California at San Francisco; *QUANTA/CHARMM* by Molecular Simulations, Inc., (1994) Burlington, Mass.; and *Insight II/Discover* by Biosysm Technologies Inc., (1994) San Diego, Calif. Other software packages will be known to those skilled in the art.

Additionally, the present invention provides methods of evaluating the binding properties of a binding compound comprising the steps of: (a) soaking a potential binding compound with GluN1 and GluN2B, to provide a crystalline GluN1 and GluN2B complexed to a binding compound; (b) determining the three-dimensional structure of the crystalline GluN1/GluN2B complexed to the binding compound by molecular replacement using the three-dimensional structure of GluN1 and GluN2B as defined by atomic coordinates available using, for example, the X-ray coordinates available via accession code 3QEL for GluN1b-GluN2BATD in complex with ifenprodil or accession code 3QEM for Ro 25-6981; and (c) analyzing the three-dimensional structure of the crystalline GluN1/GluN2B complexed to the binding compound, to the unbound binding compound to evaluate the binding characteristics of the binding compound. To evaluate binding properties of such compounds, assays may be used, such as, for example, calorimetric techniques (e.g., isothermal titration calometry, differential scanning calometry).

EXAMPLES

In order that the invention described herein may be more fully understood, the following examples are set forth. It should be understood that these examples are for illustrative purposes only and are not to be construed as limiting this invention in any manner.

Example 1

Figure 2:
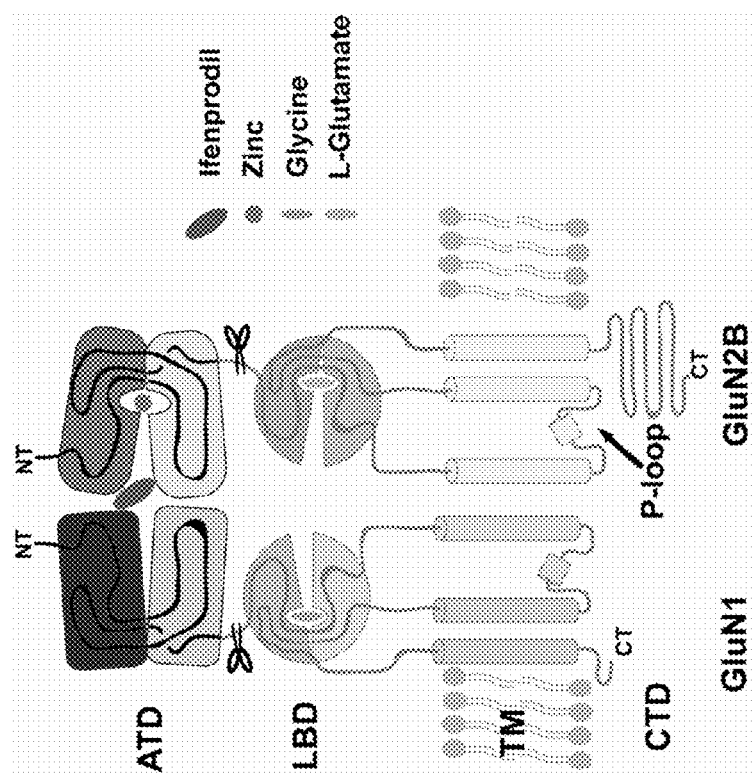
FIG. 2 depicts domain organization of NMDA receptor subunits.
Figure 3:
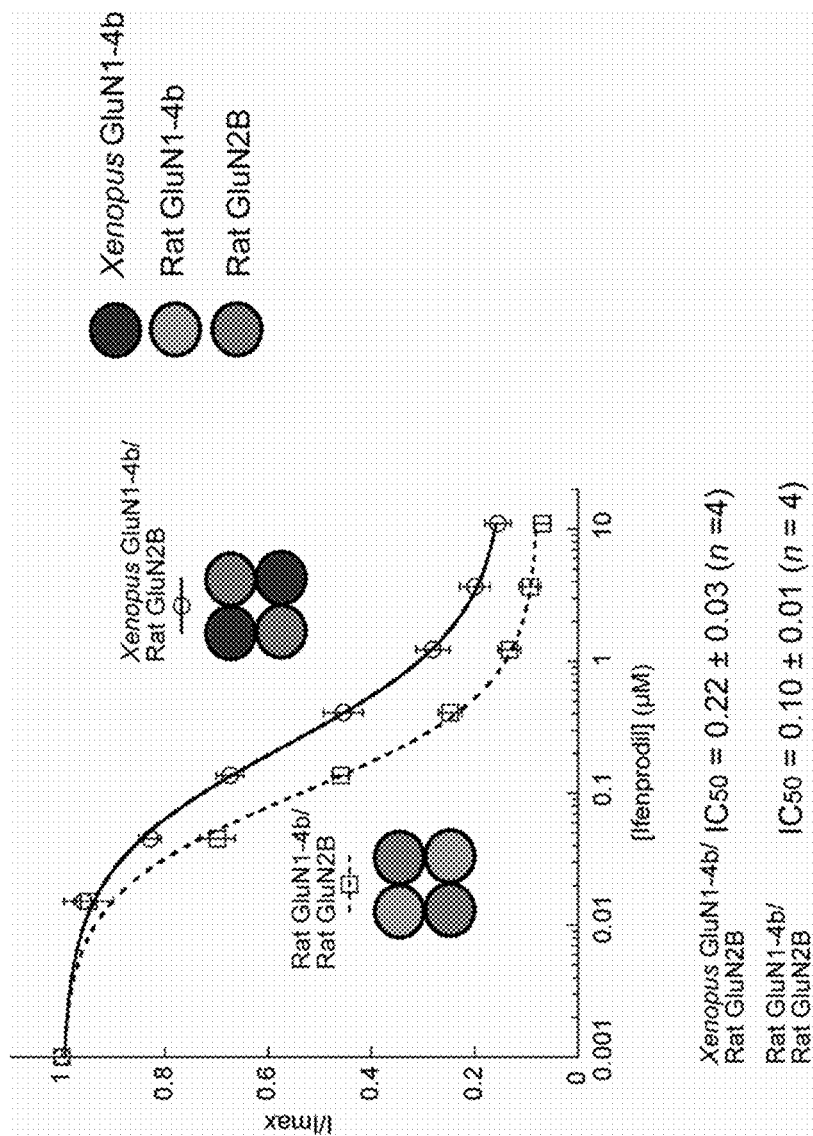
FIG. 3 shows a graph comparison of ifenoprodil sensitivity of NMDA receptors composed of rat GluN1-4b and rat GluN2B and *Xenopus* GluN1-4b and rat GluN2B.

There have been limited studies probing a direct binding of phenylethanolamine-based compounds, such as ifenprodil, to the isolated ATD of NMDA receptors. Consequently, the true requirement for receptor-compound binding has remained unclear. In order to detect direct binding of phenylethanolamine-based compounds to the ATD of the NMDA receptor, ATD proteins derived from the *Xenopus laevis* GluN1-4b (GluN1b ATD) and the *Rattus Norvegicus* GluN2B (GluN2B ATD) were recombinantly expressed, and the purified proteins were used to quantify heats resulting from direct binding of ifenprodil and Ro 25-6981 by isothermal titration calorimetry (ITC) (FIG. 1a-1b and FIG. 2). The *Xenopus laevis* GluN1-4b (Ewald et al., 2009; Schmidt et al., 2009), with superior biochemical stability over other orthologues was used in this study. It is 93% identical in primary sequence to the *Rattus Norvegicus* orthologue and is capable of forming functional NMDA receptor ion channels that undergo ifenprodil inhibition when combined with the *Rattus Norvegicus* GluN2B (FIG. 3). When the GluN1b ATD or GluN2B ATD proteins were individually injected with ifenprodil, there was no evidence of binding as no heat was created (FIG. 1a). However, when the mixture of the GluN1b and GluN2B ATD proteins were injected with ifenprodil and Ro 25-6981, heat exchange was observed in a dose-dependent manner with the $K_d$ of 320 nM and 60 nM, respectively. Thus, the above experiment showed that both GluN1b and GluN2B ATDs are required for binding of phenylethanolamine-based compounds.

To assess whether receptor-compound binding takes place in a context of heteromeric subunit arrangement, the mass of the ATD proteins in solution was determined by sedimentation experiments (FIG. 1c-1e). While individual GluN1b ATD and GluN2B ATD remained exclusively monomeric at 1.2 mg ml$^{-1}$ (FIG. 1c), they formed heterodimers at apparent $K_d$ of ~1 µM when mixed together (FIG. 1d). When ifenprodil was included in the GluN1b/GluN2B ATD protein mixture, the two subunits exclusively existed as dimers at a protein concentration as low as 0.1 mg ml$^{-1}$ (FIG. 1c and FIG. 1e). This finding showed that GluN1b and GluN2B ATDs formed heterodimers and that phenylethanolamine stabilized the GluN1b-GluN2B subunit interface.

Example 2

Figure 4:
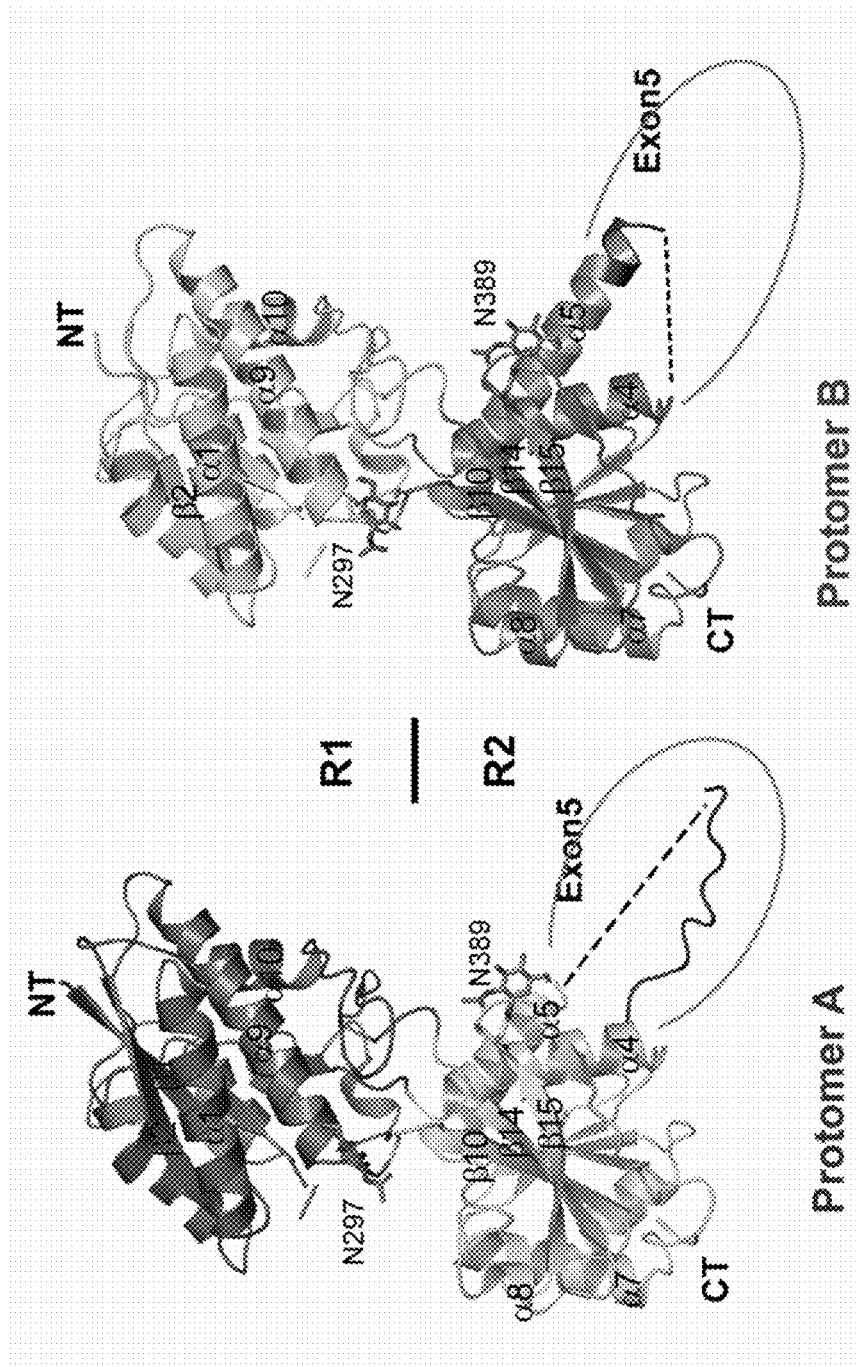
FIG. 4 depicts a crystal structure of protomers.
Figure 5:
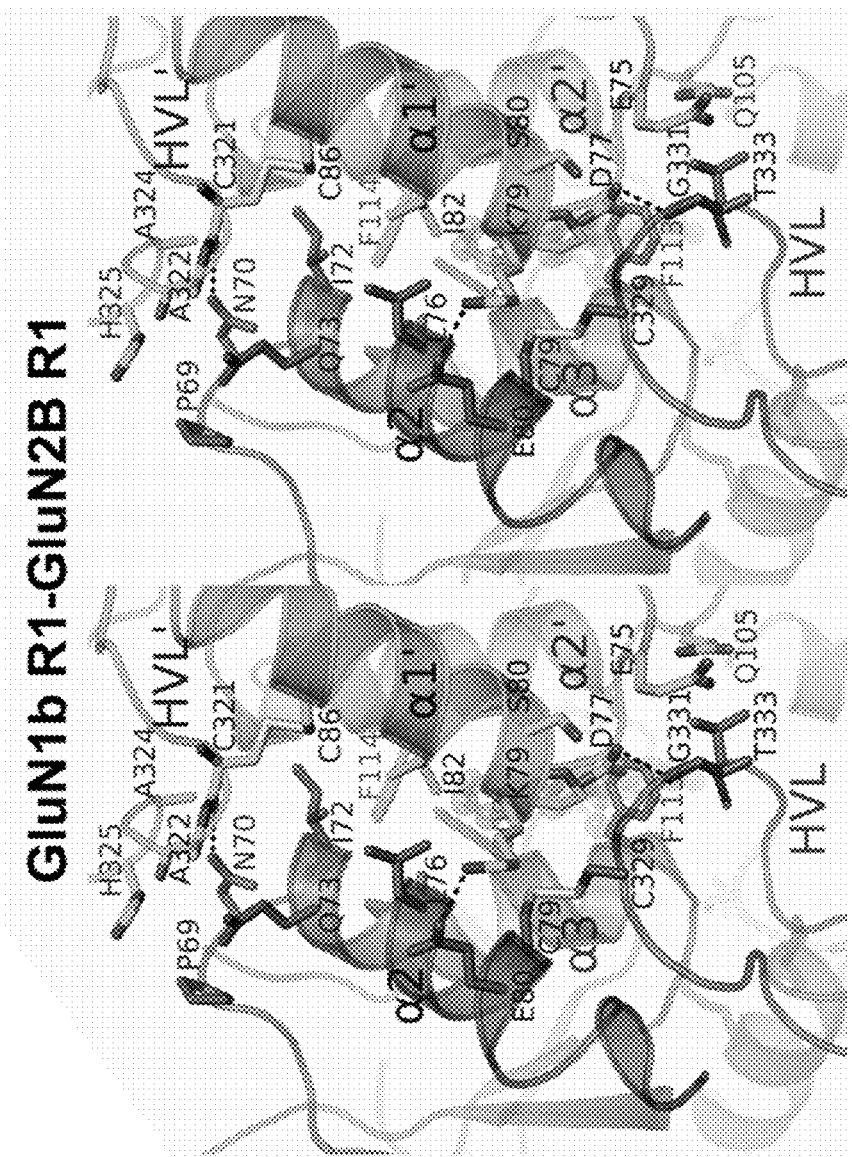
FIGS. 5 and 6 depict the crystal structure of the R1-R1 and R1-R2 interface around the ifenprodil binding site.
Figure 6:
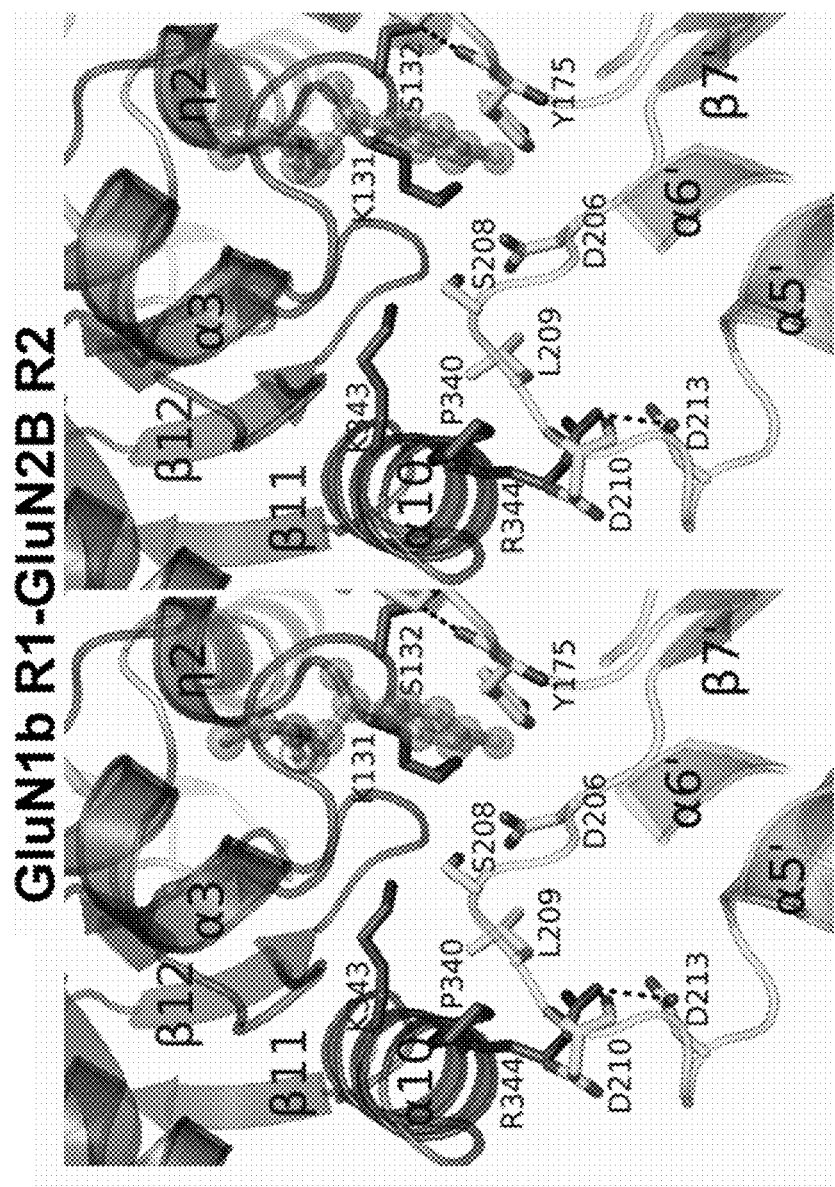
Figure 7:
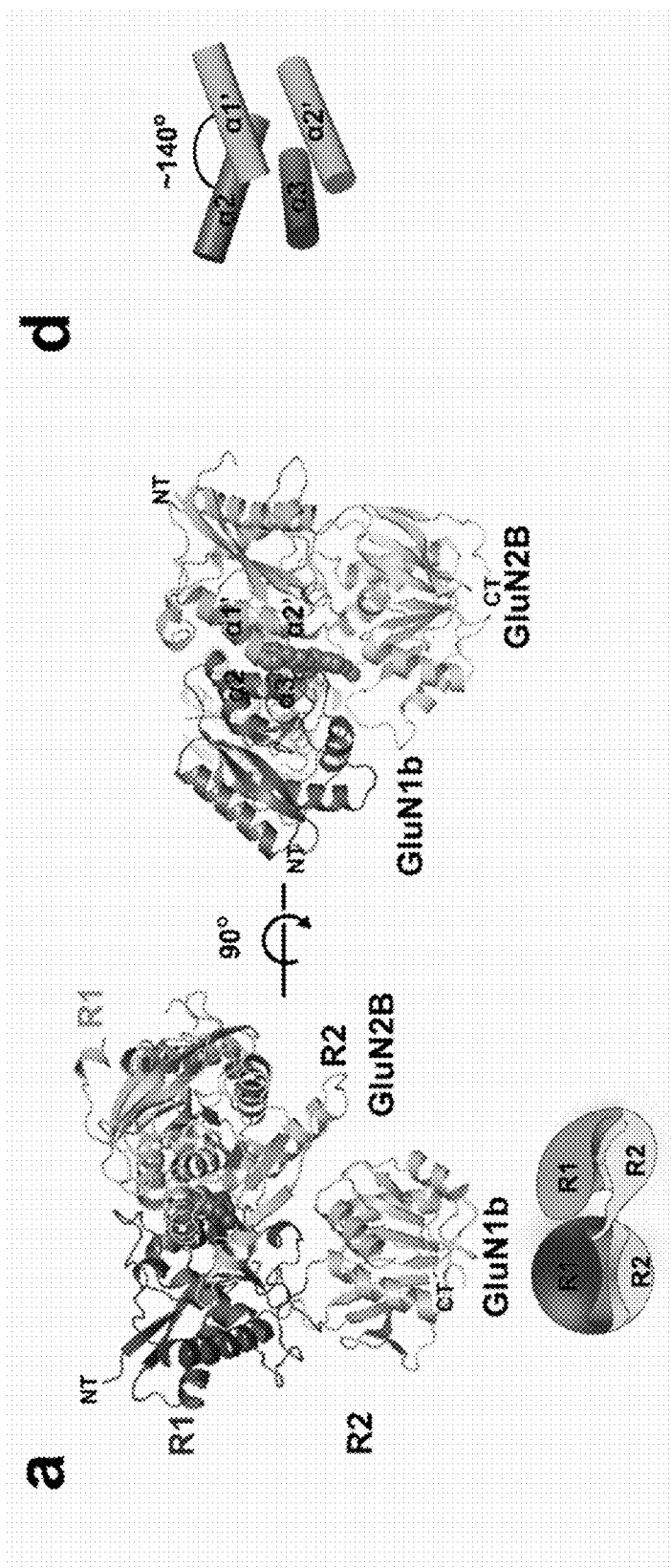
FIGS. 7a-7f depict structural comparisons of GluN1b/GluN2B ATD heterodimer and GluA2 and GluK2 ATD homodimers.
Figure 7:
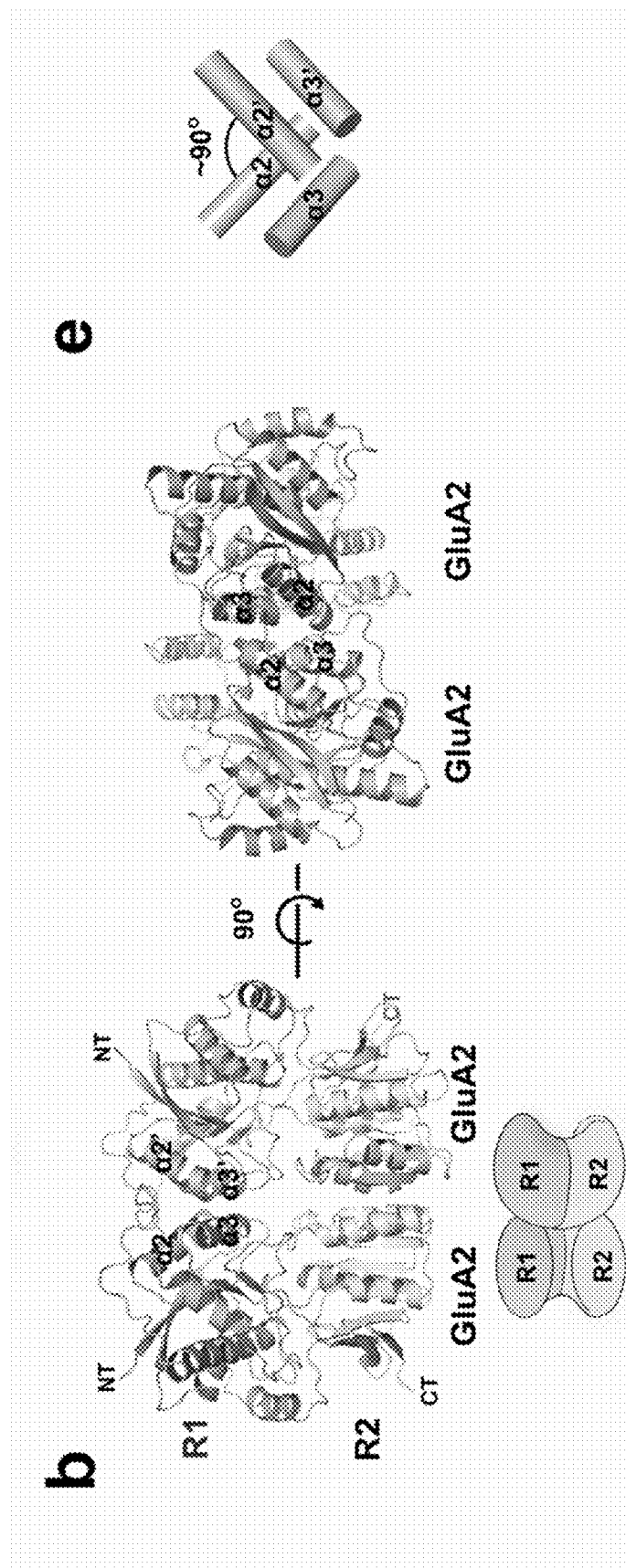
Figure 7:
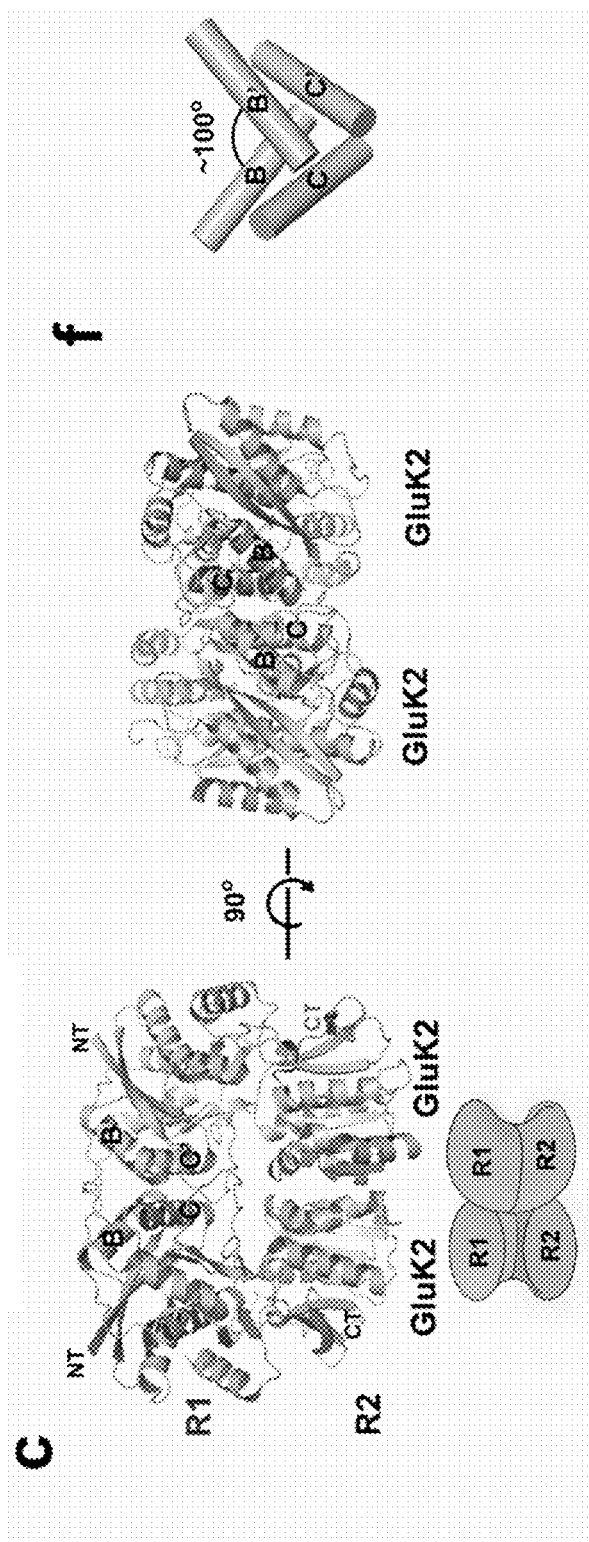

To understand the nature of the subunit interaction between GluN1b and GluN2B at ATD and to pinpoint a binding site for phenylethanolamine-based compounds on the NMDA receptor, crystallographic studies were conducted on the GluN1b/GluN2B ATD proteins. Toward this end, the structure of GluN1b ATD was first solved at 2.0 Å by a single anomalous diffraction method using seleno-methionine incorporated crystals (FIG. 4). Subsequently, the structures of GluN1b/GluN2B ATD in complex with ifenprodil and Ro 25-6981 were determined at 2.6 Å and 3.0 Å, respectively, by molecular replacement using structural coordinates of the GluN1b ATD and GluN2B ATD (Karakas et al., 2009) monomers as search probes (FIGS. 5 and 6).

Both the ifenprodil-bound and Ro 25-6981-bound crystals contained two copies of structurally similar GluN1b/GluN2B ATD heterodimers per asymmetric unit with root-mean-square (r.m.s.) deviation of 0.51 Å and 0.58 Å, respectively. Most importantly, the crystal structures clearly identified the phenylethanolamine binding site at the heterodimer interface (FIGS. 5 and 6).

Both GluN1b and GluN2B ATDs had bilobed architectures composed of R1 and R2 domains roughly similar in the secondary structure arrangement to non-NMDA receptor ATDs (Kumar et al., 2009; Jin et al., 2009; Clayton et al., 2009; Sobolevsky et al., 2009). However, the structures of NMDA receptor ATDs were not superimposable onto non-NMDA receptor ATDs due to a major difference in the R1-R2 orientations as also observed previously in the crystal structure of the GluN2B ATD monomer (Karakas et al., 2009). The unique R1-R2 orientations of the NMDA receptor ATDs resulted in a subunit arrangement highly distinct from those observed in non-NMDA receptor ATD homodimers (FIG. 7a-7f). While non-NMDA receptor ATD subunits formed symmetrical homodimers through strong R1-R1 and R2-R2 interactions, GluN1b and GluN2B ATDs associated with each other asymmetrically through R1-R1 and R1 (GluN1b)-R2 (GluN2B) interactions (FIGS. 5 and 6). No residue from GluN1b R2 were involved in the GluN1b-GluN2B interaction. The R1-R1 interface contained hydrophobic interactions through residues from the cores of α2 and α3 in GluN1b and α1' and α2' in GluN2B surrounded by polar interactions involving GluN1b α2, GluN2B α1', and hypervariable loops (HVL) (Karakas et al., 2009) (FIGS. 5 and 6). The R1-R2 interface involved mainly polar interactions involving residues on α10 and a loop extending from η2 from GluN1b and loops extending from 36' and 37' from GluN2B (FIGS. 5 and 6).

Figure 8:
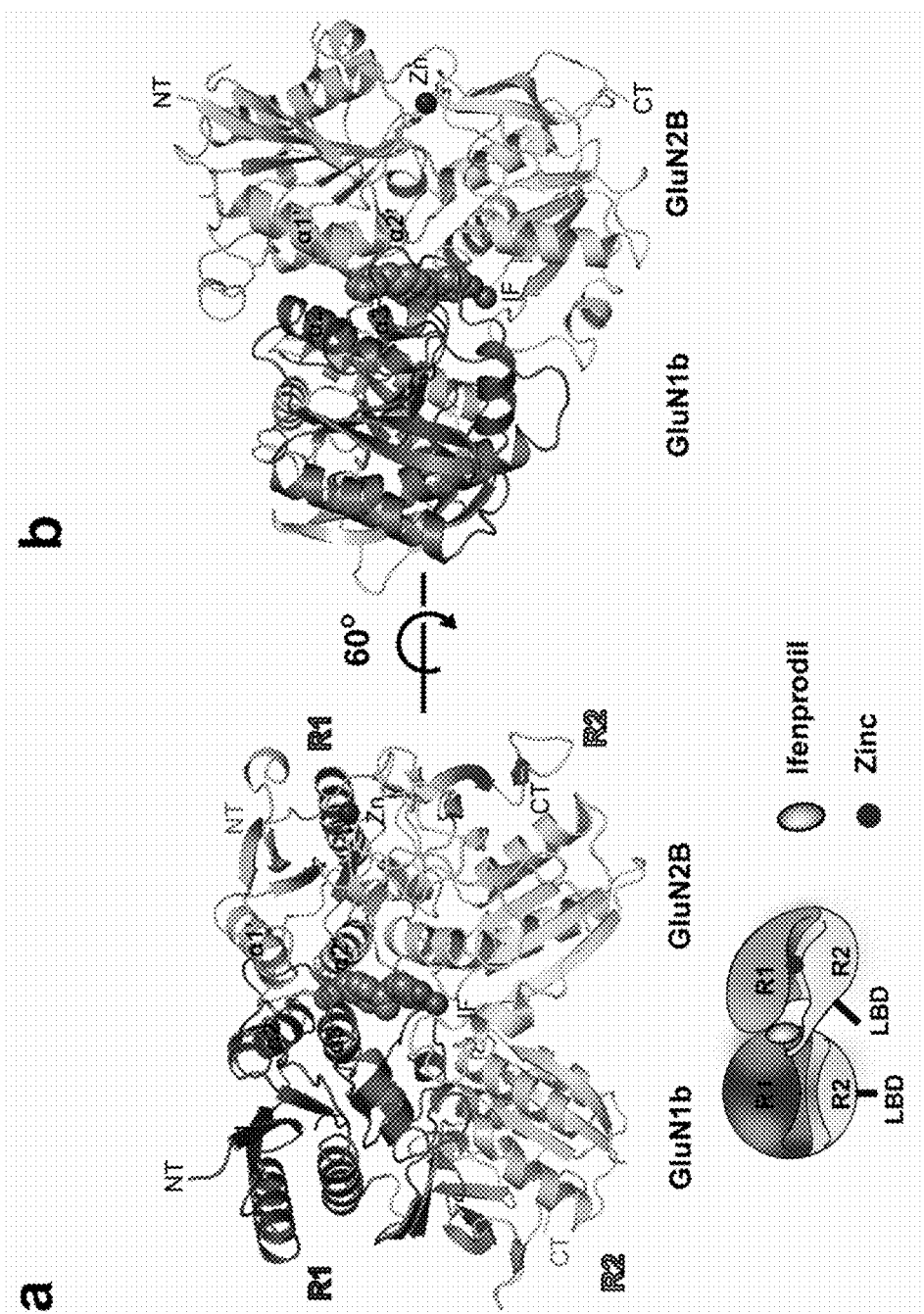
FIG. 8a-8b depicts a crystal structure showing location of zinc and ifenoprodil binding sites.
Figure 9:
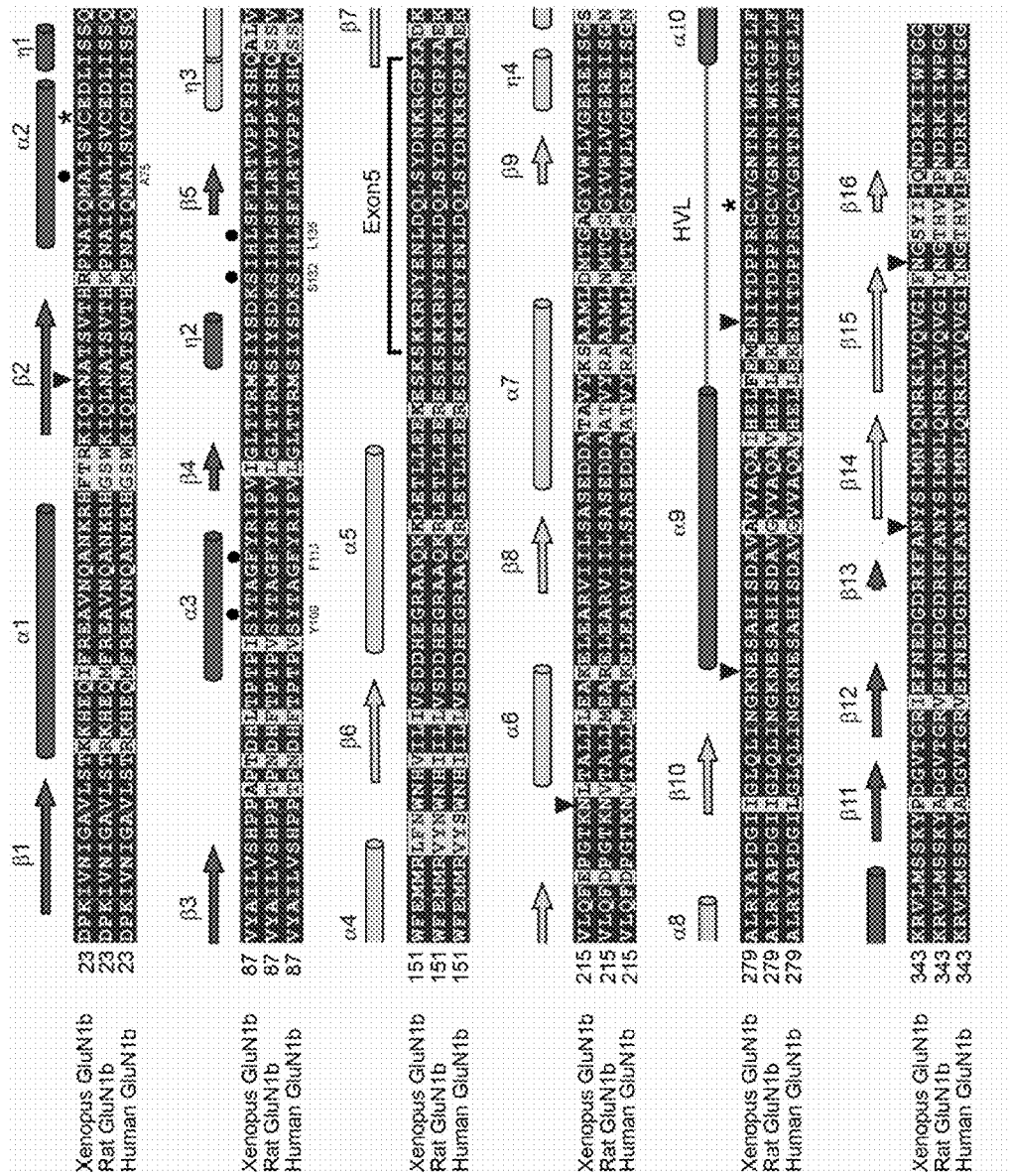
FIG. 9 show a multiple sequence alignment of GluN1b ATD from *Xenopus laevis*, rat, and human.
Figure 10:
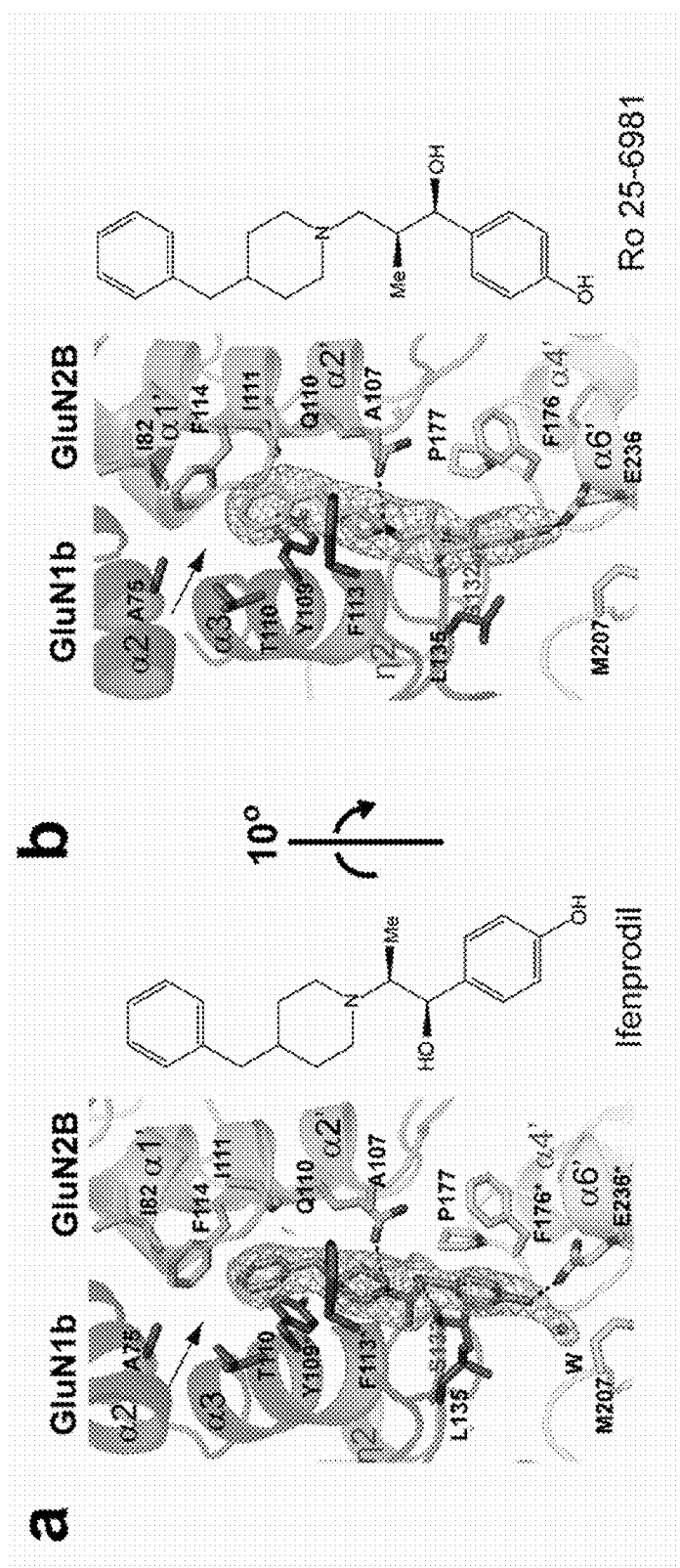
FIGS. 10a-10b depict a stereoview of the crystal structure of the phenylethanolamine binding site.
FIG. 10c depicts a stereoview comparison of binding patterns of ifenprodil and Ro 25-6981.
FIG. 10d shows a graph results of the effects of mutagenesis of binding site residues.
Figure 10:
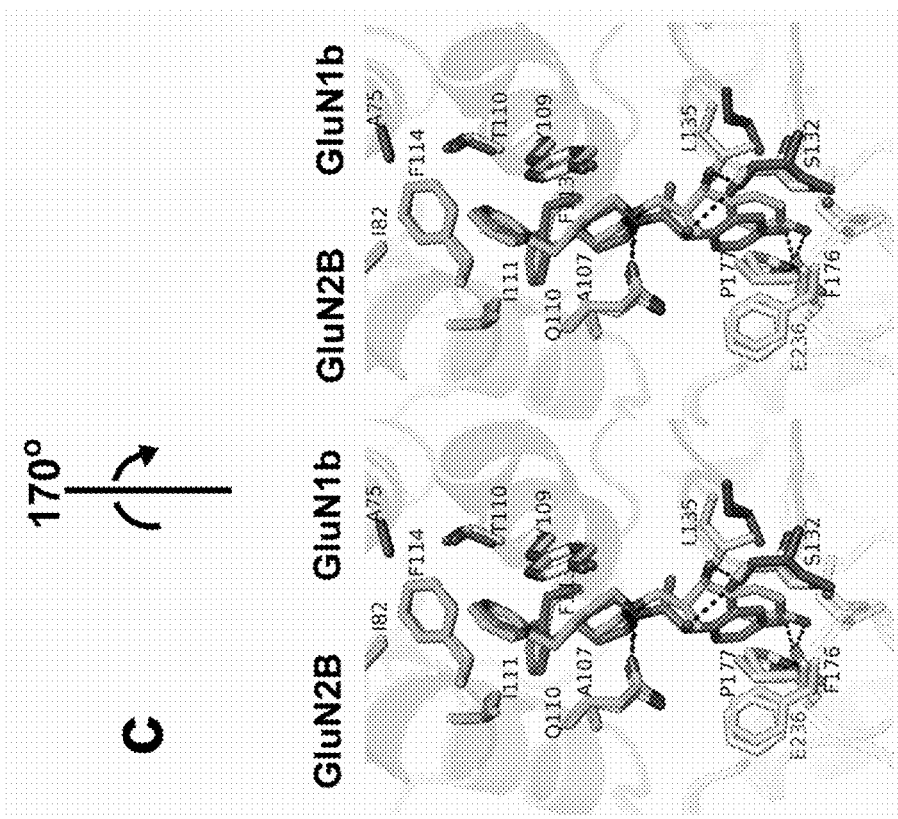
Figure 10:
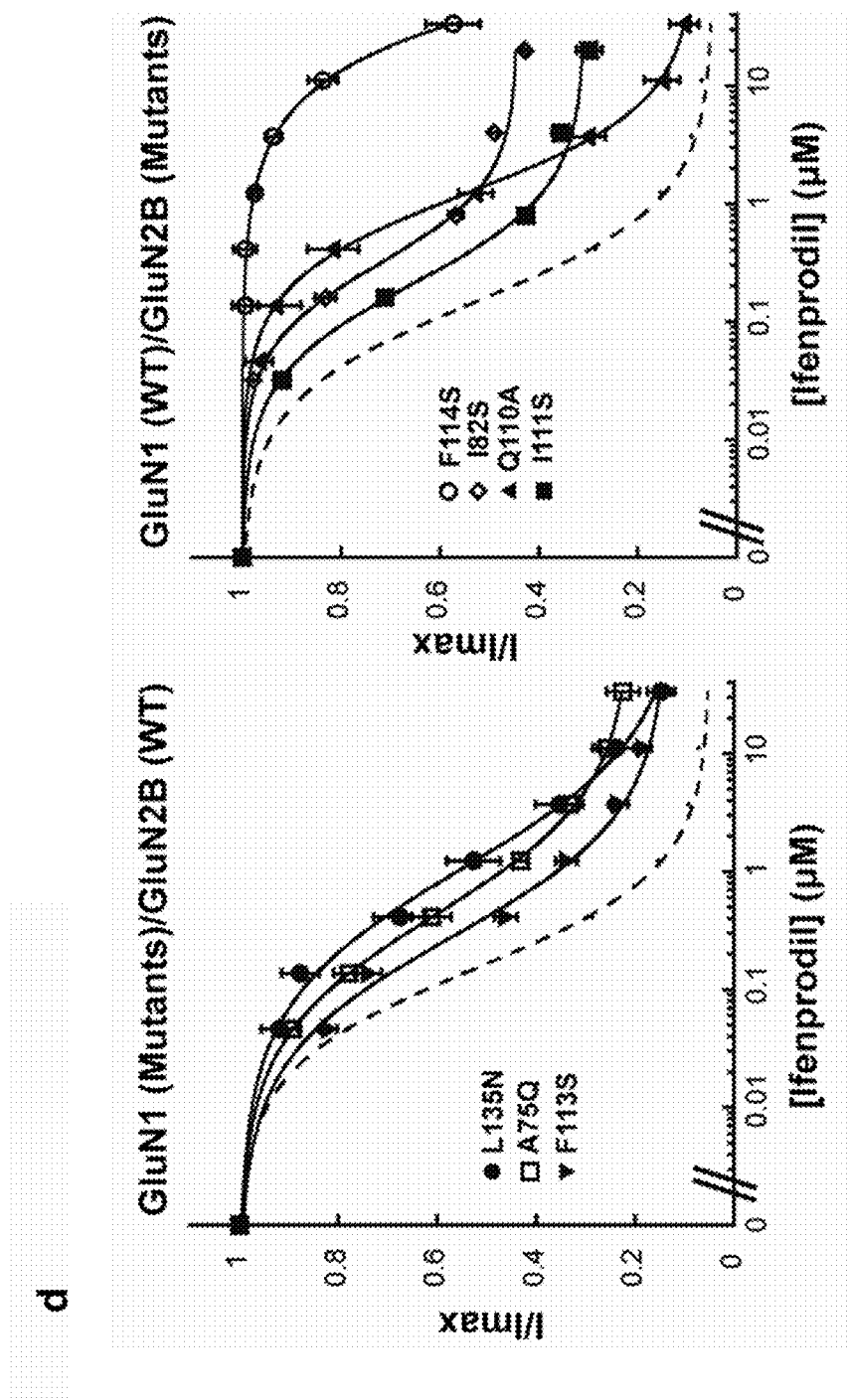

The GluN1b/GluN2B heterodimeric arrangement created for phenylethanolamine-based compounds a binding pocket composed of residues from GluN1b R1 and GluN2B R1 and R2. This binding site had no overlap with the zinc binding site that was located within the GluN2B ATD cleft (Karakas et al., 2009; Rachline et al., 2005) (FIG. 8a-8b). Nevertheless, binding of zinc and the phenylethanolamine-based compound both resulted in stabilization of the "closed" conformation of the GluN2B bilobe structure, which may result in a similar inhibitory effect (Rachline et al., 2005). The binding site for ifenprodil was occluded with no sufficient space for the ifenprodil molecule to enter or exit, which implied that the binding occurred through an induced fit mechanism and that unbinding involved opening of the GluN2B ATD bilobe structure. All of the GluN1b residues at the binding sites were identical among *Xenopus laevis*, rat, and human orthologues indicating that phenylethanolamine-based inhibition of NMDA receptors was a conserved feature among those species (FIG. 9). Binding of both ifenprodil and Ro 25-6981 was mediated mainly through hydrophobic interactions between the benzylpiperidine group and a cluster of hydrophobic residues from GluN1b α2 and α3 and GluN2B α1' and α2' and between the hydroxyl phenyl groups and GluN1b Leu135 and GluN2B Phe 176 and Pro 177 (FIG. 10a-b). Furthermore, three direct polar interactions were present between the compounds and GluN1b Ser132, GluN2B Gln110, and GluN2B Asp236. The superposition of the ifenprodil and Ro 25-6981 binding sites showed that the methyl and hydroxyl groups in the propanol moiety of both ligands face opposite directions while the benzylpiperidine groups sit in the binding pocket in the similar way (FIG. 10c). Consequently, Ro 25-6981 had a higher affinity to the NMDA receptor than ifenprodil because the methyl group in Ro 25-6981 was in a favorable position to form a hydrophobic interaction involving Phe176 and Pro177, while that in ifenprodil was in a position to form a weaker hydrophobic interaction involving L135.

Example 3

Extensive mutagenesis studies in the past have indicated GluN1b Tyr109 (Masuko et al., 1999) and GluN2B Phe176 (Perin-Dureau et al., 2002) and Asp236 (Perin-Dureau et al., 2002) to be critical in ifenprodil-inhibition. Further mutagenesis on the newly identified residues from both GluN1b and GluN2B in this study showed significant alteration in $IC_{50}$ or the extent of inhibition (FIG. 10d, Tables 1-3), confirming the physiological relevance of the binding site. Disruption of the "empty" hydrophobic space formed by GluN1b Ala75, GluN2B Ile82 and Phe114 (arrows in FIG. 10a-b) by site-directed mutations had dramatic effects on ifenprodil-sensitivity (FIG. 10d). Thus, stabilization of this hydrophobic space by filling in with a hydrophobic moiety may be a valid strategy to improve the design of phenylethanolamine-based drugs.

Figure 11:
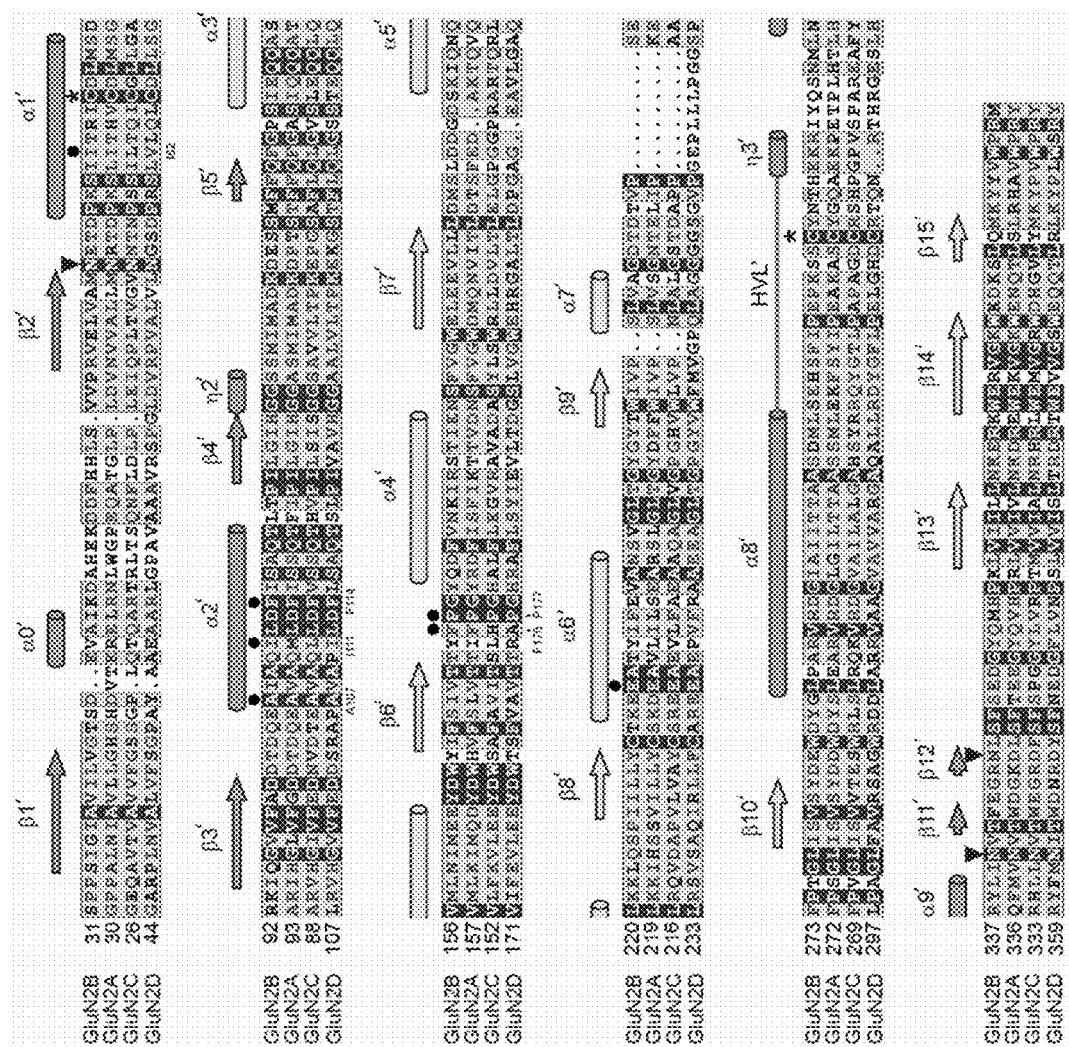
FIG. 11 shows a multiple sequence alignment of the rat GluN2 subunits within ATD.

While inspection of the primary sequences showed non-conservation of the critical binding site residues between GluN2B and GluN2C or GluN2D (such as the equivalent residue to GluN2B Phe176), all of the residues in GluN2A except GluN2B Ile111 (Met112 in GluN2A) were conserved (FIG. 11). GluN2A Met112Ile or GluN2B Ile111Met did not confer or abolish ifenprodil sensitivity in GluN1/GluN2A or GluN1/GluN2B receptors, respectively. Thus, the insensitivity of the GluN1/GluN2A receptors to phenylethanolamine may stem from a fundamental difference in a mode of subunit association between GluN1/GluN2A and GluN1/GluN2B at ATD.

TABLE 1

Data Collection

| | GluN1b ATD-Selenomethionine | GluN1b-GluN2B ATD + ifenprodil | GluN1b-GluN2B ATD + Ro 25-6981 |
|---|---|---|---|
| Space group | $P2_12_12_1$ | C2 | C2 |
| Unit cell dimensions | a = 47.3 Å, b = 92.8 Å, c = 210.0 Å | a = 268.0 Å, b = 60.9 Å, c = 144.9 Å, β = 116.5° | a = 268.0 Å, b = 61.3 Å, c = 144.4 Å, β = 116.3° |
| No. per a.u.[a] | 2 | 2 | 2 |
| Lambda (Å) | 0.9788 | 0.9795 | 1.0750 |
| $d_{min}$ (Å)[b] | 2.0 (2.07) | 2.6 (2.69) | 3.0 (3.11) |
| Total hkl | 738,798 | 188,626 | 149,647 |
| Unique hkl | 63,420 | 64,034 | 42,325 |
| I/σI[d] | 16.4 (5.9) | 13.1 (1.8) | 10.0 (2.0) |
| $R_{merge}$(%)[c,d] | 6.7 (42.3) | 7.3 (51.0) | 9.0 (63.3) |
| Completeness (%)[d] | 99.9 (100) | 98.4 (95.9) | 99.9 (100) |

[a]Number of molecules per asymmetric unit (a.u.).
[b]Values in the parentheses define the low resolution limits for the highest resolution shell of data.
[c]$R_{merge} = (\Sigma |I_i - <I_i>|)/\Sigma_i |I_i|$, where $<I_i>$ is the mean $I_i$ over symmetry-equivalent reflections.
[d]Values in parentheses are lor the highest resolution shell of data.

TABLE 2

Refinement Statistics

| | GluN1b ATD | GluN1b-GluN2B ATD + ifenprodil | GluN1b-GluN2B ATD + Ro 25-6981 |
|---|---|---|---|
| Resolution (Å) | 30.0-2.0 | 30.0-2.6 | 30.0-3.0 |
| Number of reflections | 117,186 | 59,854 | 40,132 |
| $R_{work}$ | 19.2 | 18.8 | 19.2 |
| $R_{free}$[a] | 22.7 | 23.8 | 25.0 |
| No of atoms | 6,002 | 10,760 | 10,278 |
| Protein | 5,576 | 10,416 | 10,095 |
| NAG | 84 | 112 | 98 |
| BMA | 11 | 11 | 11 |
| Fucose | — | 10 | — |
| Mannose | — | 22 | 22 |
| Sodium | — | 2 | 2 |
| Potassium | 2 | — | — |
| Ifenprodil | — | 48 | — |
| Ro 25-6981 | — | — | 50 |
| Water | 329 | 139 | — |
| Wilson B factor (Å²) | 32.2 | 49.4 | 65.2 |
| B factor (Å²) | | | |
| Protein | 38.2 | 72.1 | 78.8 |
| NAG | 62.7 | 72.9 | 84.4 |
| BMA | 70.6 | 57.1 | 68.1 |
| Fucose | — | 72.6 | — |
| Mannose | — | 65.1 | 72.1 |
| Sodium | — | 56.4 | 82.8 |

TABLE 2-continued

Refinement Statistics

|  | GluN1b ATD | GluN1b-GluN2B ATD + ifenprodil | GluN1b-GluN2B ATD + Ro 25-6981 |
|---|---|---|---|
| Potassium | 27.5 | — | — |
| Ifenprodil | — | 49.2 | — |
| Ro 25-6981 | — | — | 51.5 |
| Water | 39.5 | 52.5 | — |
| Rms deviations |  |  |  |
| Bond length(Å) | 0.01 | 0.01 | 0.01 |
| Bond angles(°) | 1.07 | 1.13 | 1.24 |
| Ramachandran statistics (%)[b] |  |  |  |
| Favored | 98.4 | 95.4 | 91.0 |
| Allowed | 1.6 | 3.8 | 9.0 |
| Outliers | — | — | — |

[a]5% of the reflections are set aside for calculation of $R_{free}$ value.
[b]Ramachandran statistics are calculated using Molprobity (Davis et al., 2007)
Davis, I. W., Leaver-Fay, A., Chen, V. B., Block, J. N., Kapral, G. J., Wang, X., Murray, L. W., Arendall, W. B. III, Snoeyink, J., Richardson J. S., and Richardson D. C. (2007). MolProbity: all-atom contacts and structure validation for proteins and nucleic acids. Nucleic Acids Research 35, W375-W383.

TABLE 3

Ifenprodil dose-response on wild type and mutant GluN1/GluN2B receptors

| GluN1/GluN2B Receptors | Ifenprodil $IC_{50}$ (μM) | % inhibition | n |
|---|---|---|---|
| Wild type |  |  |  |
| GluN1-1a (WT)/GluN2B (WT) | 0.12 ± 0.03 | 95.0 ± 2.5 | 8 |
| GluN1-1b (WT)/GluN2B (WT) | 0.16 ± 0.02 | 95.2 ± 2.0 | 8 |
| GluN1 mutants |  |  |  |
| GluN1-1b (A75Q)/GluN2B (WT) | 0.46 ± 0.08 | 82.1 ± 1.4 | 5 |
| GluN1-1b (F113S)/GluN2B (WT) | 0.28 ± 0.03 | 87.7 ± 1.4 | 5 |
| GluN1-1b (L135N)/GluN2B (WT) | 1.15 ± 0.32 | 90.0 ± 3.7 | 5 |
| GluN2B mutants |  |  |  |
| GluN1-1b (WT)/GluN2B (I82S) | 0.31 ± 0.03 | 55.7 ± 0.7 | 4 |
| GluN1-1b (WT)/GluN2B (Q110A) | 1.21 ± 0.11 | 91.5 ± 2.2 | 6 |
| GluN1-1b (WT)/GluN2B (I111M) | 0.23 ± 0.02 | 93.0 ± 2.2 | 5 |
| GluN1-1b (WT)/GluN2B (I111S) | 0.21 ± 0.02 | 69.3 ± 2.6 | 5 |
| GluN1-1a (WT)/GluN2B (F114S) | <10 μM | N.D. | 5 |
| GluN1-1a (WT)/GluN2B (F114A) | <10 μM | N.D. | 5 |

$IC_{50}$ and % inhibition values are shown in mean ± s.d. and n is the number of *Xenopus* oocytes from which recordings are made.

Example 4

Figure 12:
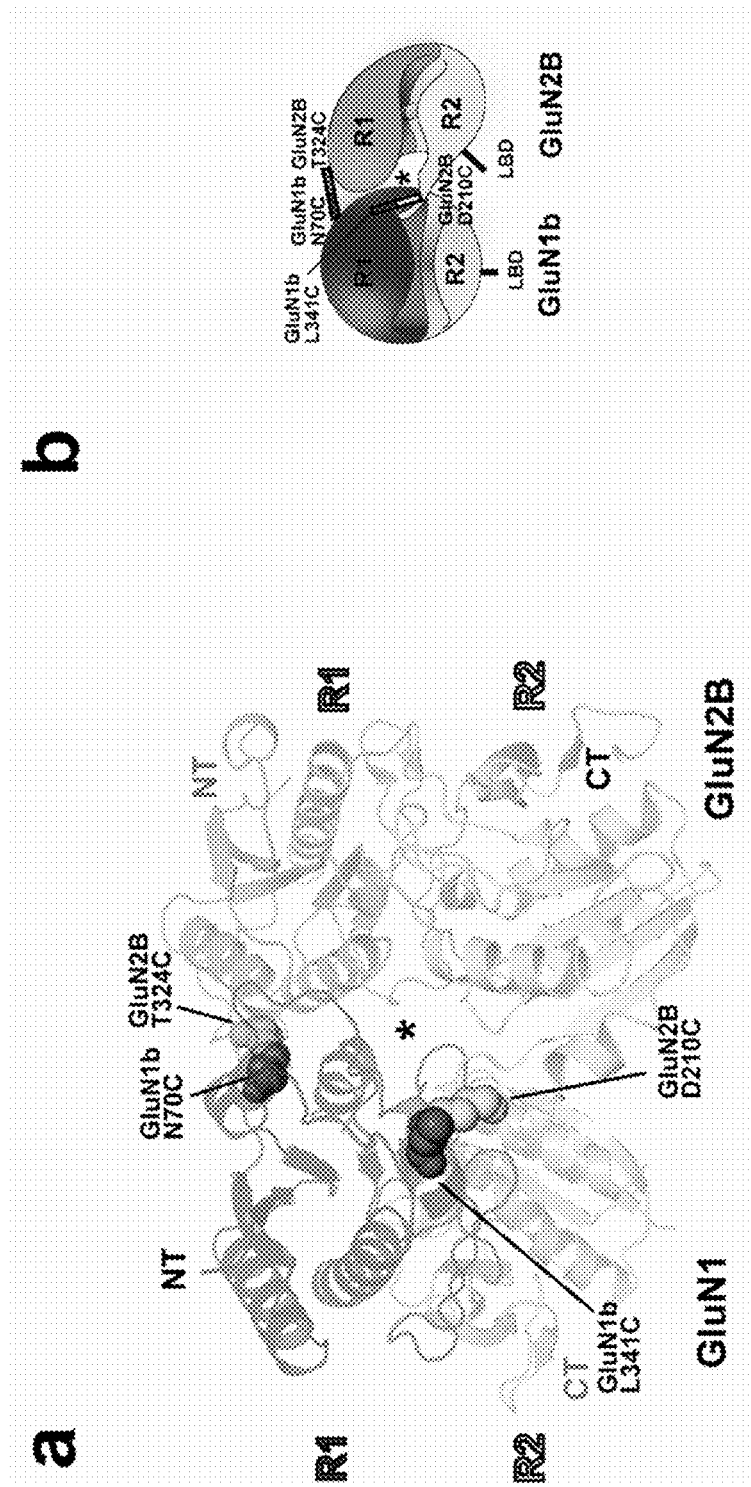
FIG. 12a depicts a crystal structure showing the location of mutated residues at the GluN1b-GluN2B interface at ATD.
FIG. 12b depicts the location of mutated residues at the GluN1b-GluN2B interface at ATD.
FIG. 12c shows an observation of disulphide bonds by western blot.
FIG. 12d shows a current recording of mutant receptors in the presence and absence of DTT.
FIG. 12e shows the effect of disulphide bonds on ifenprodil sensitivity.
FIG. 12f depicts a possible model of ifenprodil binding and movement of ATD that may couple to allosteric inhibition.
Figure 12:
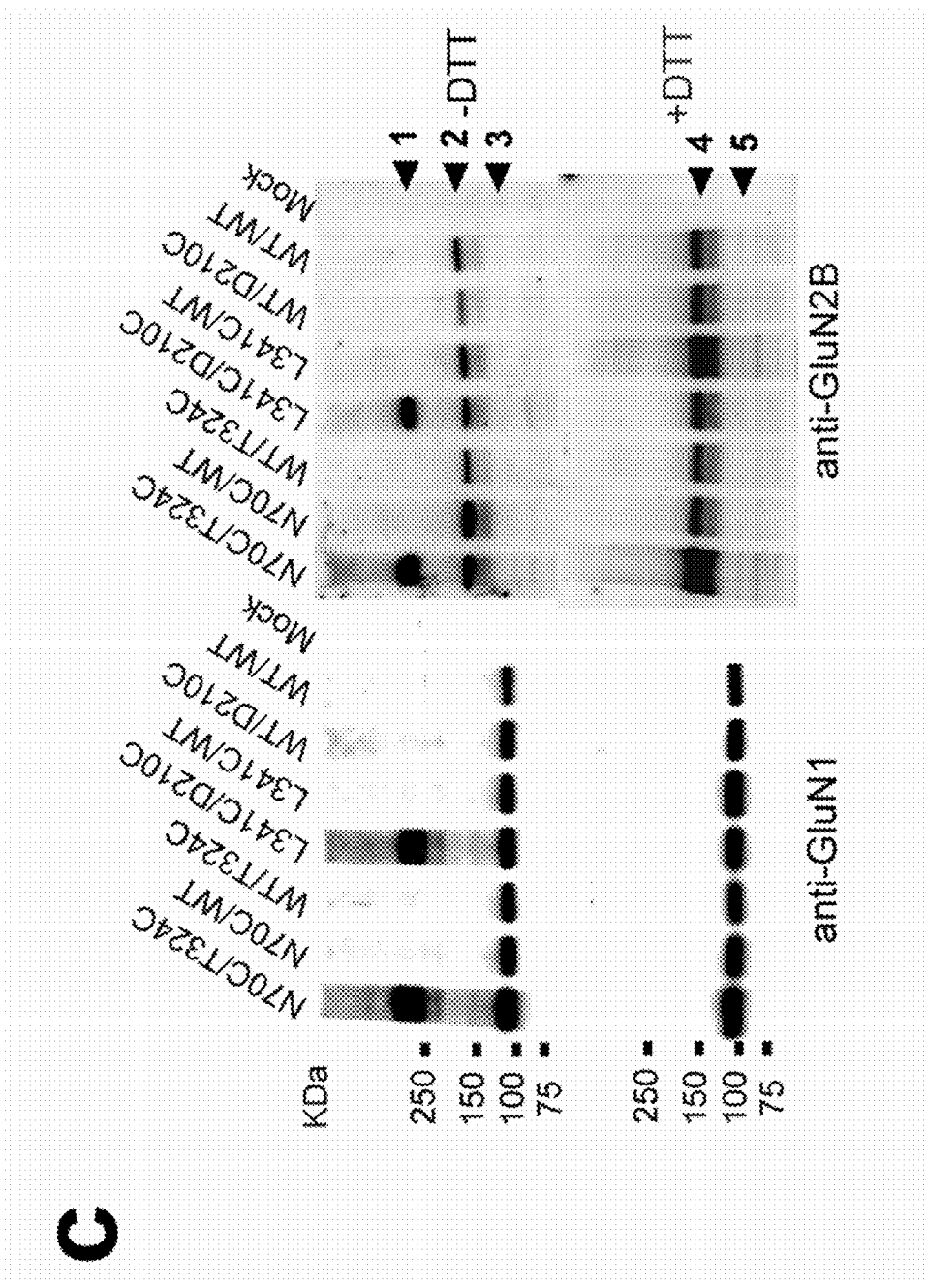
Figure 12:
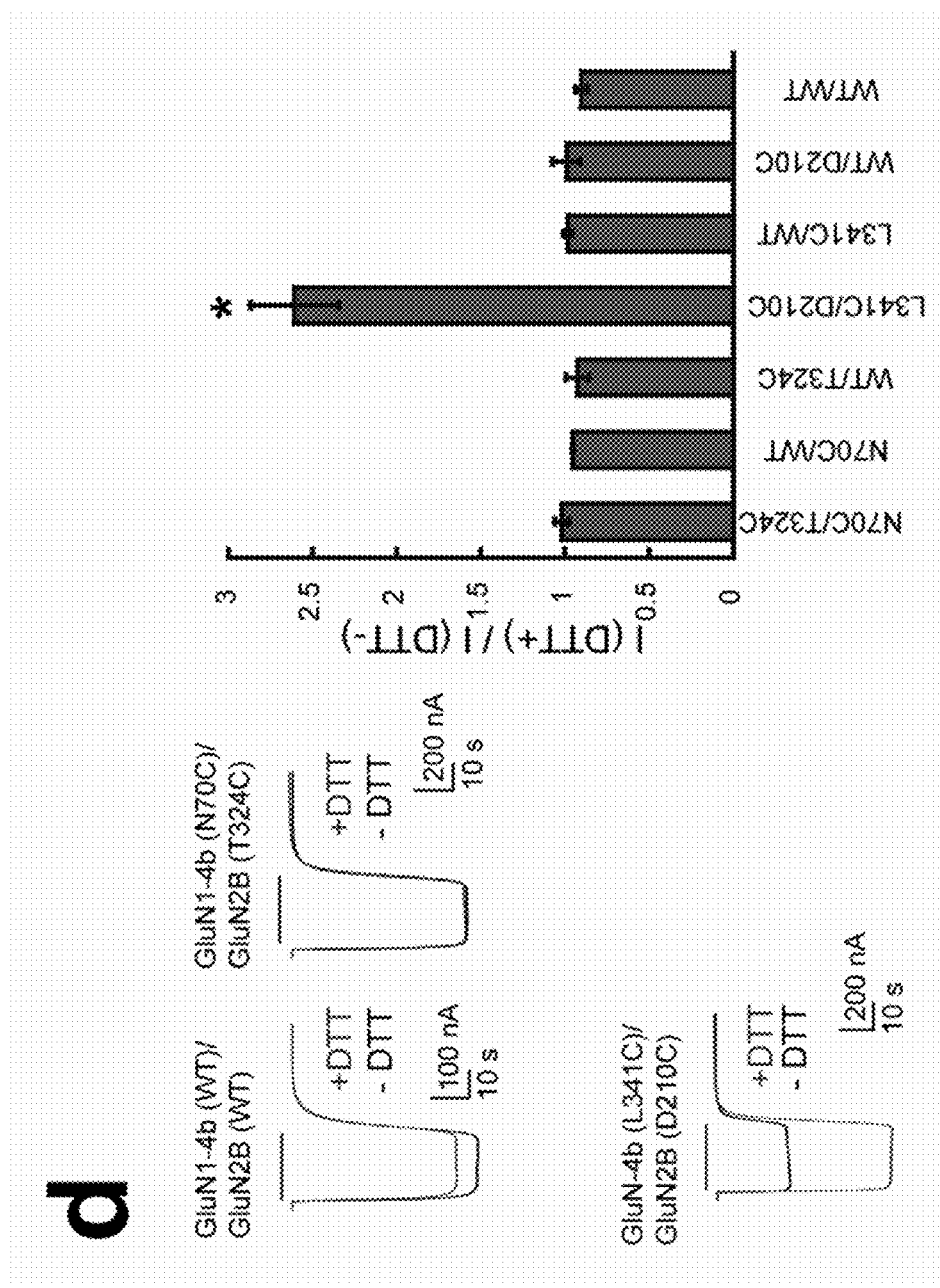
Figure 12:
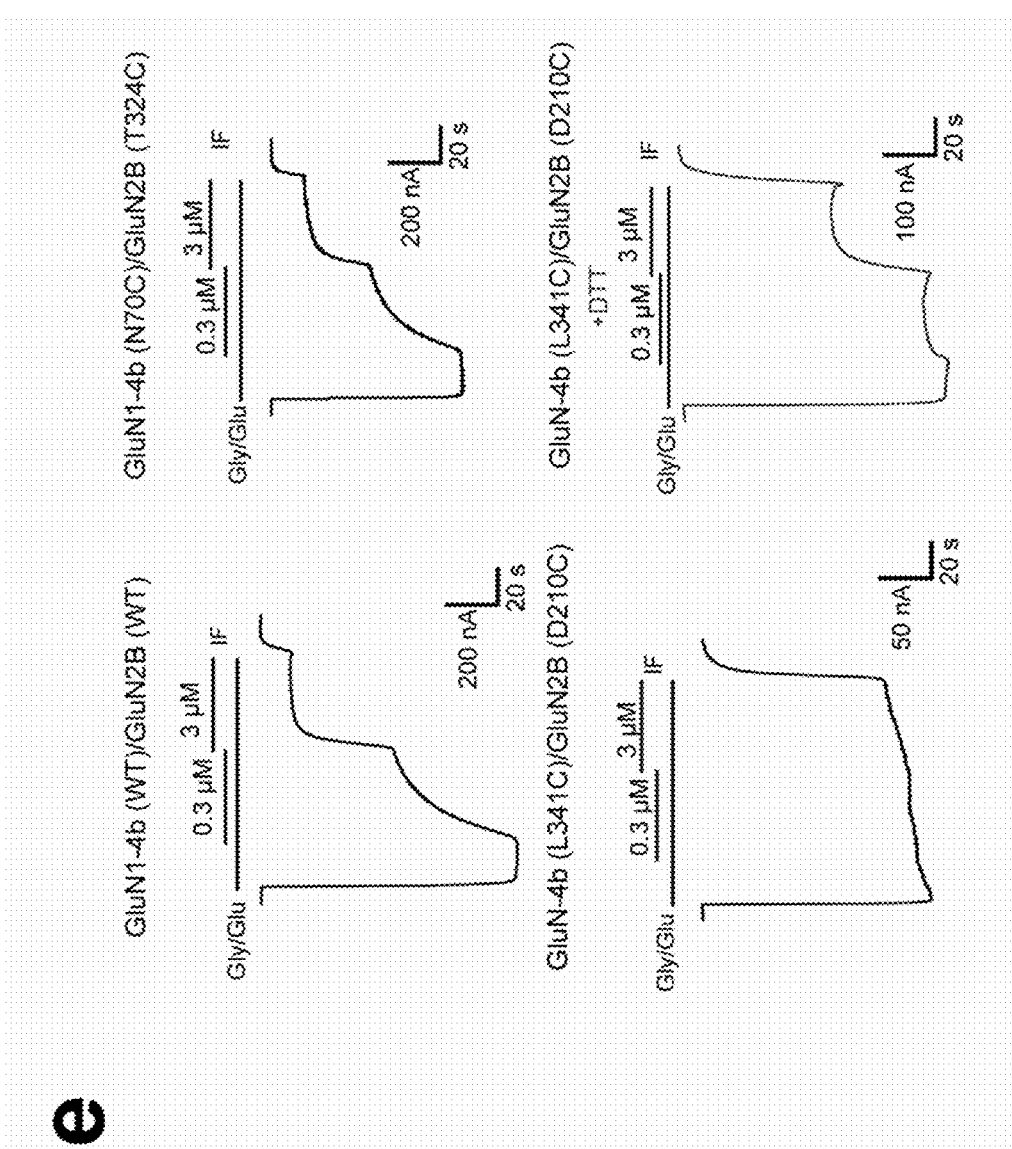
Figure 12:
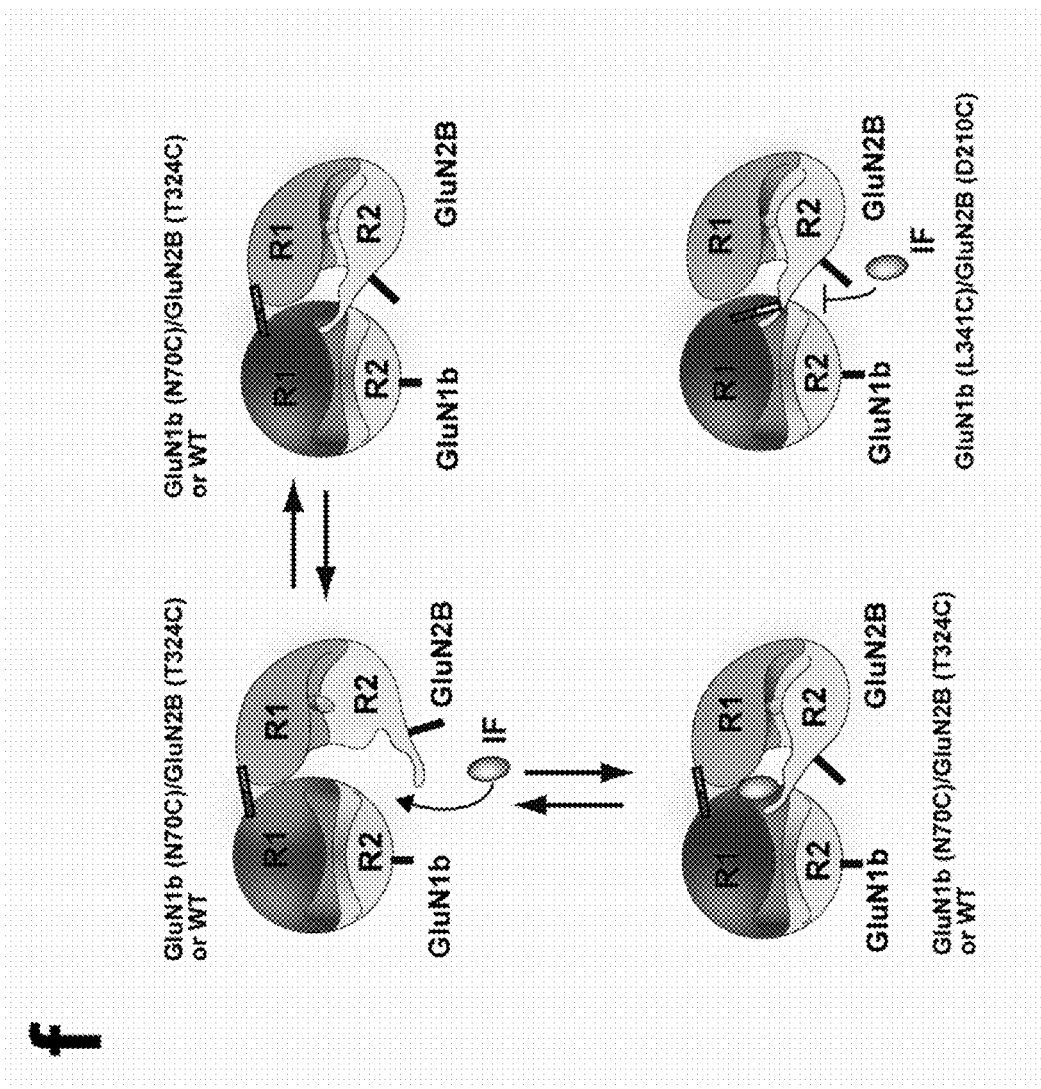
Figure 13:
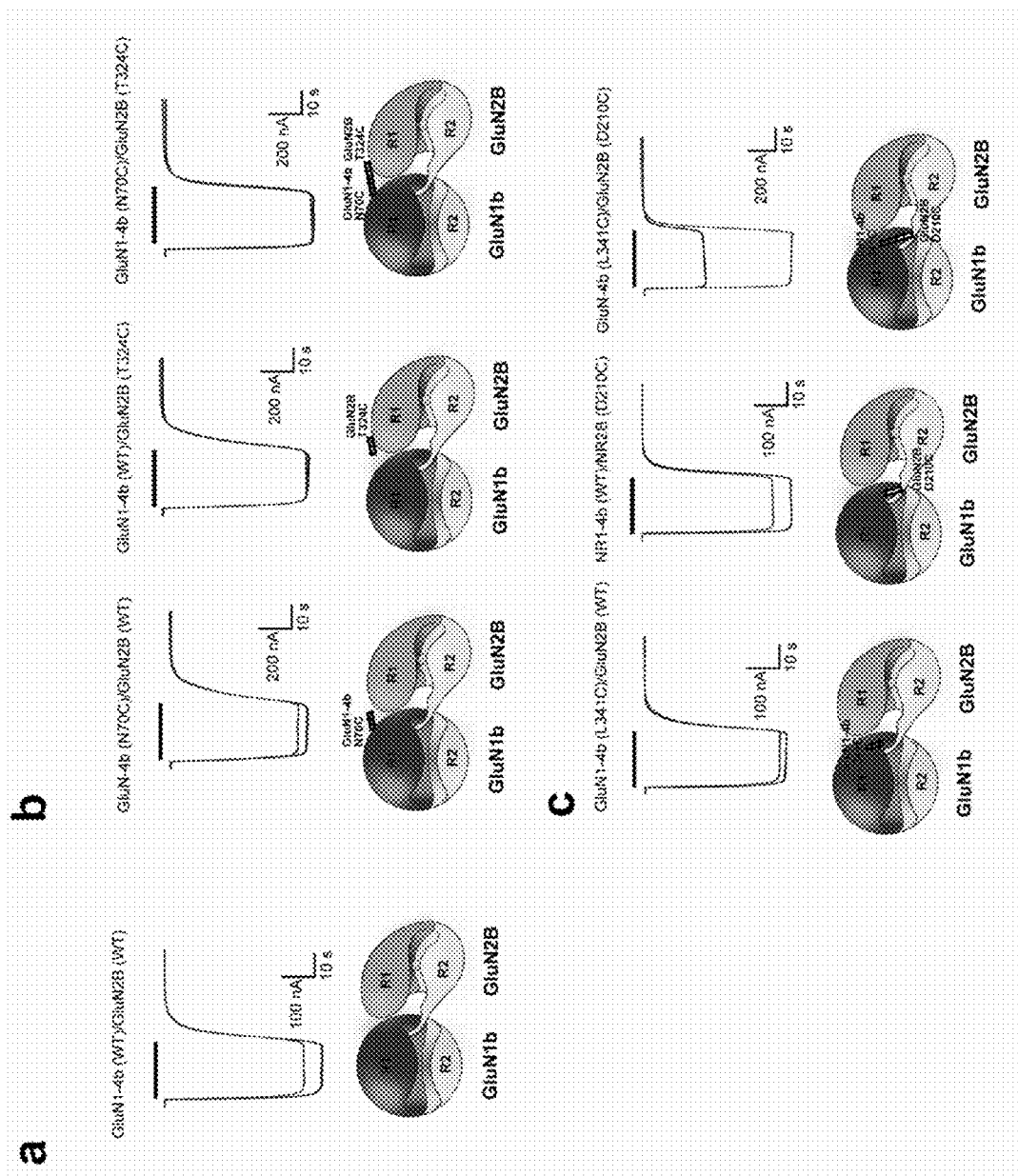
FIGS. 13a-13c depict current recordings showing the effect of DTT application on the cystenine mutant and wild type GluN1-4b and GluN2B receptors.
Figure 14:
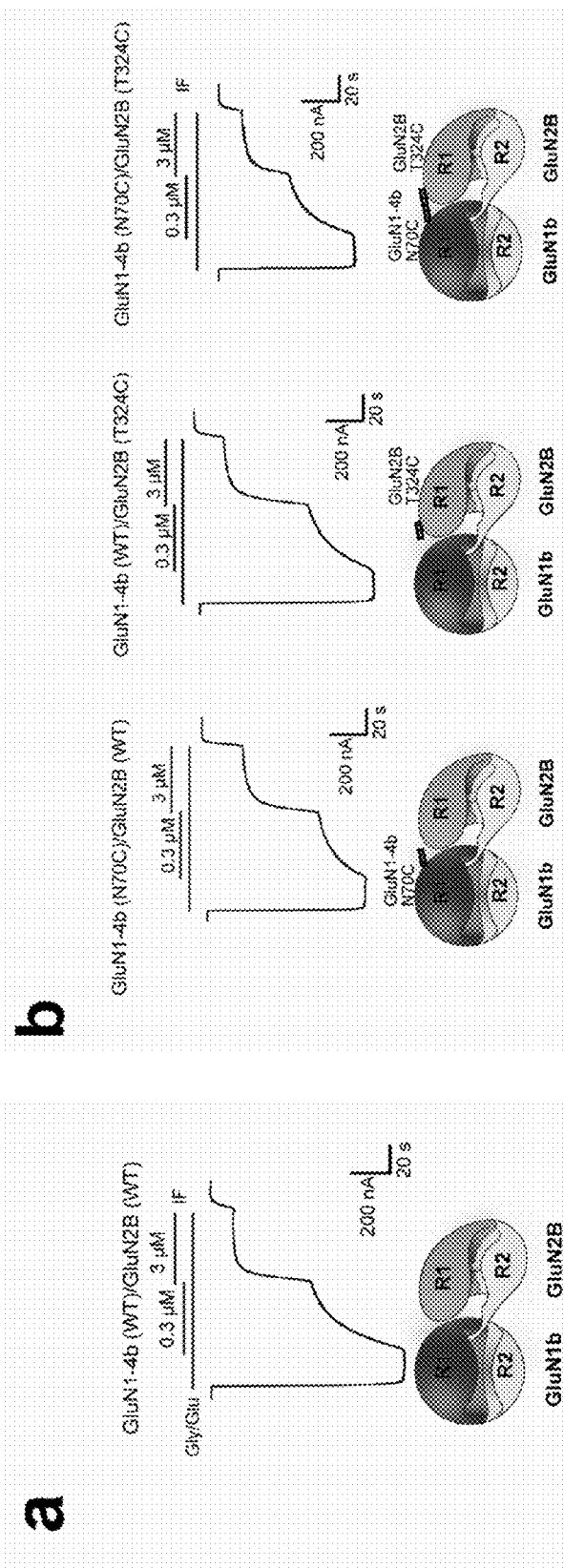
FIGS. 14a-14c depicts current recordings showing ifenoprodil-sensitivity on the cysteine mutant and wild type GluN1-4b and GluN2B receptors.
FIG. 14d depicts a graph of average current recording from four individual oocytes.
Figure 14:
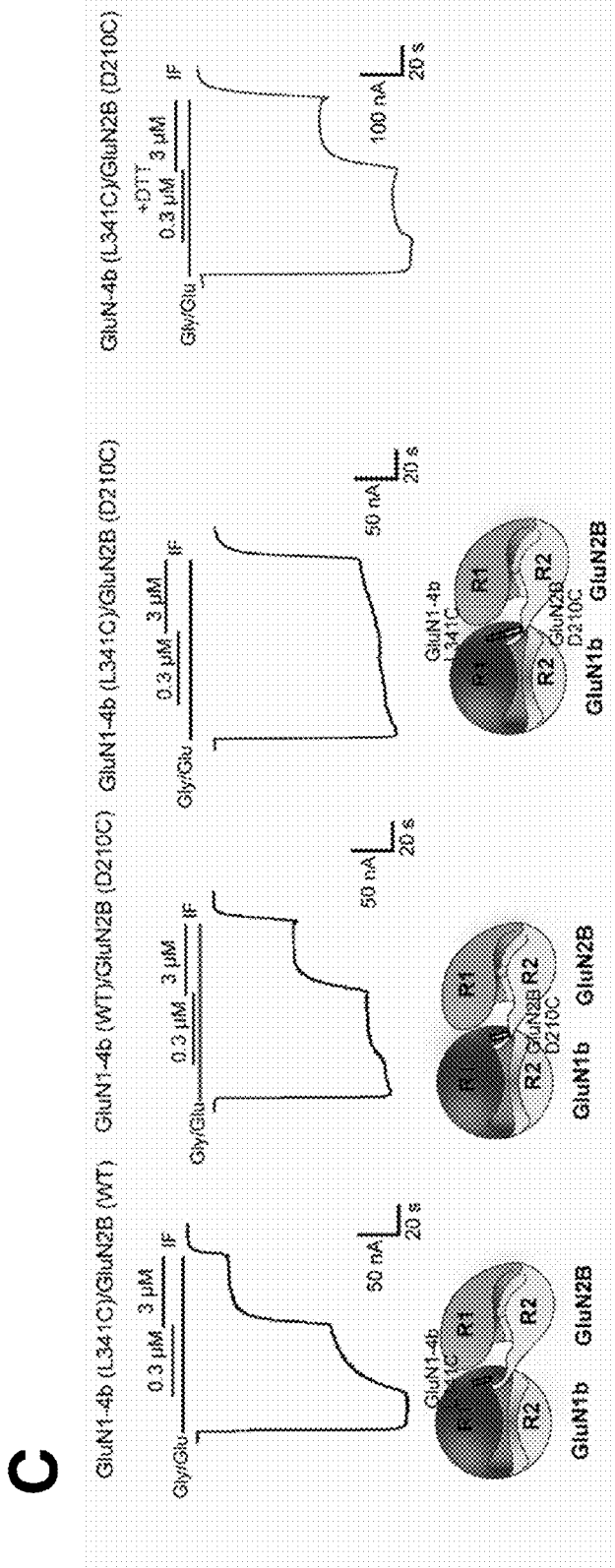
Figure 14:
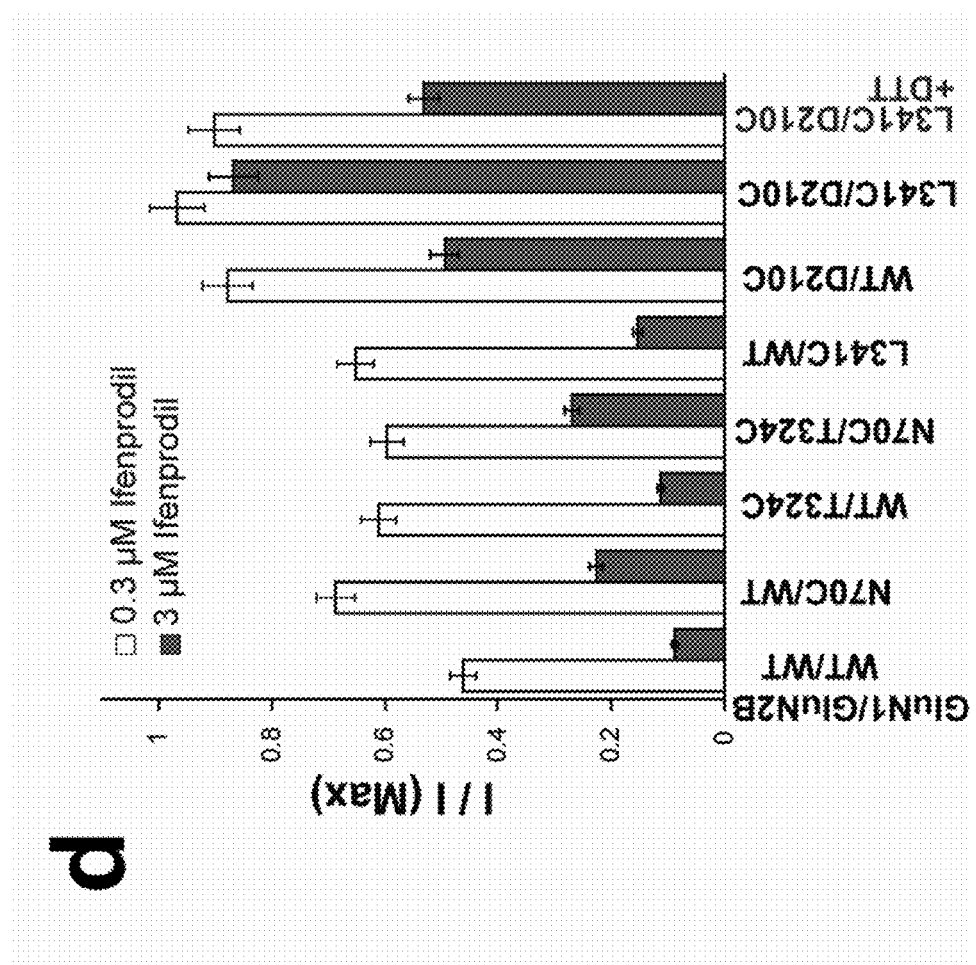

To further validate the physiological relevance of the hetero-dimeric assembly, cysteine mutants at the subunit interface were engineered using the ifenprodil-bound GluN1b/GluN2B ATD structure as a guide in a context of the intact rat GluN1-4b/GluN2B receptors so that they would form spontaneous disulphide bonds if the mutated residues are proximal to each others. Toward this end, two pairs of cysteine mutants, GluN1-4b (Asn70Cys)/GluN2B (Thr324Cys) and GluN1-4b (Leu341Cys)/GluN2B (Asp210Cys) were designed, which "locked" the R1-R1 and R1-R2 interfaces, respectively FIG. 12a-b). The mutant receptors were then expressed in a mammalian cell culture, and analyzed for formation of disulphide-linked oligomers in western blots. When mutant receptors of one subunit were expressed with wild-type receptors of the other, they gave rise to monomeric bands (110 KDa and 170 KDa for GluN1-4b and GluN2B, respectively; arrow 2 and 3) identical to the wild-type GluN1-4b/GluN2B receptors in both reducing and non-reducing condition. In contrast, co-expressing pairs of the GluN1-4b/GluN2B cysteine mutants gave rise to a heterodimeric ~280 KDa band recognized by both anti-GluN1 and anti-GluN2B antibodies in non-reducing condition (FIG. 12c, arrow 1). This confirmed that the heterodimeric arrangement of GluN1b and GluN2B ATDs with the R1-R1 and R1-R2 subunit interfaces is physiological and that the heterodimer, but not the homodimer, is a basic functional unit in ATD, as in the case of non-NMDA receptors. Furthermore, the disulphide cross-linking was observed in the presence and absence of ifenprodil indicating that the ligand-free GluN1b/GluN2B ATDs may oscillate between the previously suggested open conformation and closed conformation represented by the current crystal structure.

Example 5

To understand the functional effects of "locking" the R1-R1 and R1-R2 interactions in the GluN1b/GluN2B ATDs, the ion channel activities of the cysteine mutant receptors were measured by TEVC. First, the effect of breaking the disulphide bonds on ion channel activity was explored. Application of DTT has a minor inhibitory effect on the wild-type GluN1-4b/GluN2B receptors unlike the potentiating effect previously observed in the GluN1-1a/GluN2B receptors (Choi et al., 2001). By contrast, a 2.5-fold potentiation was observed upon breakage of the GluN1-4b (Leu341Cys)-GluN2B (Asp210Cys) disulphide bond at the R1-R2 interface (FIG. 12d and FIG. 13a-c). This implied that "locking" the closed conformation in the GluN2B ATD bilobe structure by the R1-R2 cross-link resulted in down-regulation of the ion channel activity. The effect of the disulphide bonds on ifenprodil sensitivity was next tested. While the R1-R1 cross-link had only a minor effect, the R1-R2 cross-link almost completely abolished ifenprodil inhibition, even at 3 μM (FIG. 12e). When this R1-R2 disulphide cross-link was broken by an application of DTT, the mutant receptors regain sensitivity to ifenprodil to a similar extent to that observed in GluN1-4b (WT)/GluN2B (D210C) in a non-reducing condition (FIG. 12e, FIG. 13a-c). This indicated that ifenprodil cannot bind GluN1b/GluN2B ATD when the R1-R2 interaction is "locked" and thus, when the GluN2B ATD bilobe is closed. Taken together, the experiments above impled that binding of ifenprodil requires an opening of the GluN2B bilobed structure and that ifenprodil inhibition involves a closure of the bilobe through the GluN1b R1-GluN2B R2 interaction (FIG. 12f).

The current study showed that the binding of phenylethanolamine occurs at the GluN1/GluN2B subunit through an induced-fit mechanism and that the allosteric inhibition involved stabilization of the GluN2B ATD bilobe structure in a closed conformation. The binding mechanism presented here provided an atomic blueprint for improving designs of therapeutic compounds targeting NMDA receptor ATD.

Example 6

Compounds of Formula (I) may be synthesized according to the procedure described in Chenard et al., *J. Med. Chem.* (1991) 34:3085, e.g., coupling of an alpha-bromo ketone and an amine, followed by reduction as depicted in Scheme 1.

Scheme 1.

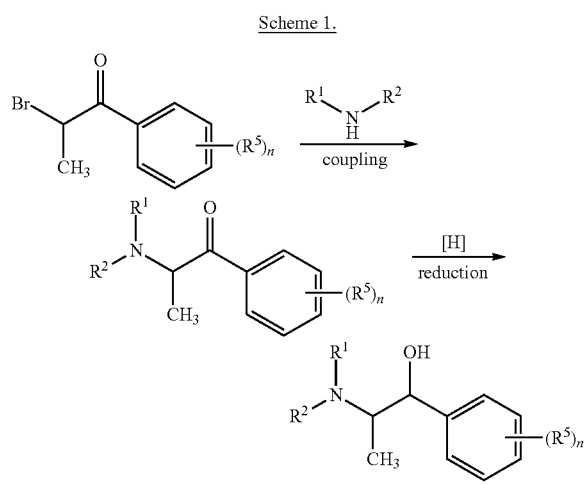

REFERENCES

Gotti, B. et al. Ifenprodil and SL 82.0715 as cerebral anti-ischemic agents. I. Evidence for efficacy in models of focal cerebral ischemia. *J. Pharmacol. Exp. Ther.* 247, 1211-1221 (1988).

Koller, M. & Urwyler, S, Novel N-methyl-D-aspartate receptor antagonists: a review of compounds patented since 2006. *Expert Opin. Ther. Pat.* 20, 1683-1702 (2010).

Hansen, K. B., Furukawa, H. & Traynelis, S. F. Control of assembly and function of glutamate receptors by the amino-terminal domain. *Mol. Pharmacol.* 78, 535-549 (2010).

Mony, L., Kew, J. N., Gunthorpe, M. J. & Paoletti, P. Allosteric modulators of NR2B containing NMDA receptors: molecular mechanisms and therapeutic potential. *Br. J. Pharmacol.* 157, 1301-1317 (2009).

Traynelis, S. F. et al. Glutamate receptor ion channels: structure, regulation, and function. *Pharmacol. Rev.* 62, 405-496 (2010).

Gallagher, M. J., Huang, H., Pritchett, D. B. & Lynch, D. R. Interactions between ifenprodil and the NR2B subunit of the N-methyl-D-aspartate receptor. *J. Biol. Chem.* 271, 9603-9611 (1996).

Williams, K. Ifenprodil discriminates subtypes of the N-methyl-D-aspartate receptor: selectivity and mechanisms at recombinant heteromeric receptors. *Mol. Pharmacol.* 44, 851-859 (1993).

Ewald, R. C. & Cline, H. T. Cloning and phylogenetic analysis of NMDA receptor subunits NR1, NR2A and NR2B in *Xenopus laevis* tadpoles. *Front. Mol. Neurosci.* 2,4 (2009).

Schmidt, C. & Hollmann, M. Molecular and functional characterization of *Xenopus laevis* N-methyl-D-aspartate receptors. *Mol. Cell. Neurosci.* 42, 116-127 (2009).

Karakas, E., Simorowski, N. & Furukawa, H. Structure of the zinc-bound aminoterminal domain of the NMDA receptor NR2B subunit. *EMBO J.* 28, 3910-3920 (2009).

Kumar, J., Schuck, P., Jin, R. & Mayer, M. L. The N-terminal domain of GluR6-subtype glutamate receptor ion channels. *Nature Struct. Mol. Biol.* 16, 631-638 (2009).

Jin, R. et al. Crystal structure and association behaviour of the GluR2 aminoterminal domain. *EMBO J.* 28, 1812-1823 (2009).

Clayton, A. et al. Crystal structure of the GluR2 aminoterminal domain provides insights into the architecture and assembly of ionotropic glutamate receptors. *J. Mol. Biol.* 392, 1125-1132 (2009).

Sobolevsky, A. I., Rosconi, M. P. & Gouaux, E. X-ray structure, symmetry and mechanism of an AMPA-subtype glutamate receptor. *Nature* 462, 745-756 (2009).

Gielen, M., Siegler Retchless, B., Mony, L., Johnson, J. W. & Paoletti, P. Mechanism of differential control of NMDA receptor activity by NR2 subunits. *Nature* 459, 703-707 (2009).

Rachline, J., Perin-Dureau, F., Le Goff, A., Neyton, J. & Paoletti, P. The micromolar zinc-binding domain on the NMDA receptor subunit NR2B. *J. Neurosci.* 25, 308-317 (2005).

Malherbe, P. et al. Identification of critical residues in the amino terminal domain of the human NR2B subunit involved in the RO 25-6981 binding pocket. *J. Pharmacol. Exp. Ther.* 307, 897-905 (2003).

Masuko, T. et al. A regulatory domain (R1-R2) in the amino terminus of the N-methyl-D-aspartate receptor: effects of spermine, protons, and ifenprodil, and structural similarity to bacterial leucine/isoleucine/valine binding protein. *Mol. Pharmacol.* 55, 957-969 (1999).

Perin-Dureau, F., Rachline, J., Neyton, J. & Paoletti, P. Mapping the binding site of the neuroprotectant ifenprodil on NMDA receptors. *J. Neurosci.* 22, 5955-5965 (2002).

Lee, C. H. & Gouaux, E. Amino terminal domains of the NMDA receptor are organized as local heterodimers. *PLoS ONE* 6, e19181 (2011).

Adams, P. D. et al. PHENIX: building new software for automated crystallographic structure determination. *Acta Crystallogr. D* 58, 1948-1954 (2002).

Other Embodiments

All patents, patent applications, and literature references cited herein are incorporated herein by reference.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

The foregoing has been a description of certain non-limiting embodiments of the invention. Those of ordinary skill in the art will appreciate that various changes and modifications to this description may be made without departing from the spirit or scope of the present invention, as defined in the following claims.

What is claimed is:

1. A method of therapeutically treating an NMDA-mediated disorder comprising administering to a subject in need thereof a compound of Formula (I-c):

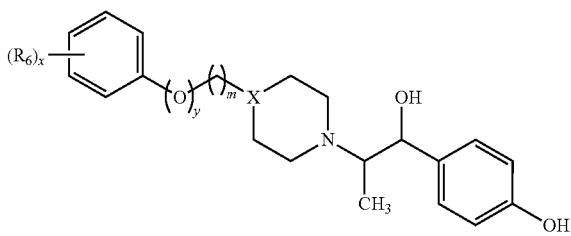

(I-c)

or a pharmaceutically acceptable salt thereof,
wherein:
X is CH;
each instance of $R_6$ is independently selected from the group consisting of substituted hydroxyl, substituted thio, silyl, halo, optionally substituted alkyl, optionally substituted alkenyl, optionally substituted alkynyl, optionally substituted carbocyclyl, optionally substituted heterocyclyl, optionally substituted aryl, and optionally substituted heteroaryl, provided at least two $R_6$ groups ortho to each other are joined to form an optionally substituted pyrrolyl ring;
x is an integer between 2 and 5, inclusive;
y is 0 or 1; and
m is 1 or 2;
wherein the compound stabilizes the molecular conformation of hydrophobic residues GluN1b A74, GluN2B I82, and GluN2B F114 of the NMDA receptor; and
wherein the NMDA-mediated disorder is selected from the group consisting of Alzheimer's disease and Parkinson's disease.

2. The method of claim 1, wherein the compound physically interacts with the hydrophobic residues GluN1b A74, GluN2B I82, and GluN2B F114 of the NMDA receptor, thereby partially or completely inhibiting NMDA receptor function.

3. The method of claim 1, wherein the compound is of formula (I-f):

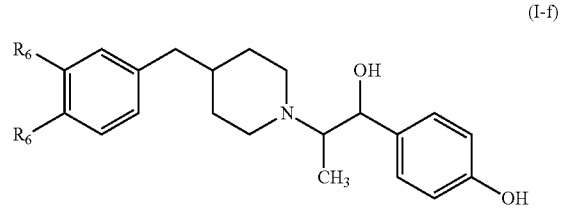

(I-f)

or a pharmaceutically acceptable salt thereof,
wherein the two $R_6$ groups ortho to each other are joined to form an optionally substituted pyrrolyl ring.

4. The method of claim 1, wherein the compound is:

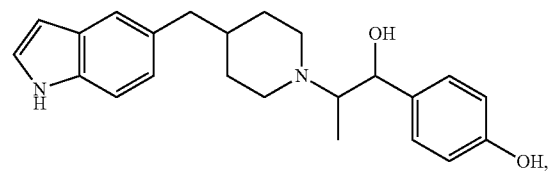 [SMILES: CC(C(O)c1ccc(O)cc1)N1CCC(Cc2ccc3[nH]ccc3c2)CC1]

or a pharmaceutically acceptable salt thereof.

* * * * *